United States Patent
Topfer et al.

(10) Patent No.: US 10,039,516 B2
(45) Date of Patent: Aug. 7, 2018

(54) DIGITAL RADIOGRAPHY DETECTOR IMAGE READOUT SYSTEM AND PROCESS

(71) Applicant: Carestream Health, Inc., Rochester, NY (US)

(72) Inventors: Karin Topfer, Rochester, NY (US); John DeHority, Rochester, NY (US); Jeffrey R. Hawver, Marion, NY (US)

(73) Assignee: Carestream Health, Inc., Rochester, NY (US)

( * ) Notice: Subject to any disclaimer, the term of this patent is extended or adjusted under 35 U.S.C. 154(b) by 576 days.

(21) Appl. No.: 14/534,737

(22) Filed: Nov. 6, 2014

(65) Prior Publication Data

US 2015/0131785 A1 May 14, 2015

Related U.S. Application Data

(60) Provisional application No. 61/901,699, filed on Nov. 8, 2013.

(51) Int. Cl.
*A61B 6/00* (2006.01)
*G06T 5/00* (2006.01)
(Continued)

(52) U.S. Cl.
CPC .......... *A61B 6/5258* (2013.01); *A61B 6/4233* (2013.01); *A61B 6/5205* (2013.01);
(Continued)

(58) Field of Classification Search
CPC ......... G01T 7/005; G06K 9/40; G06T 7/0065; G06T 7/0097; G06T 5/50; G06T 5/002; G06T 2207/10124; G06T 2207/20224; G06T 2207/10144; G06T 2207/10116; G06T 2207/20182; G06T 2207/20221; G06T 2207/30004; H04N 5/32; H04N 5/361; H04N 5/3597; H04N 5/3205; H04N 5/3651; H04N 5/357; H04N 5/359;
(Continued)

(56) References Cited

U.S. PATENT DOCUMENTS

| 5,818,898 A | 10/1998 | Tsukamoto et al. |
| 5,912,942 A * | 6/1999 | Schick ............ G01T 1/2018 250/370.09 |

(Continued)

FOREIGN PATENT DOCUMENTS

| EP | 2 293 111 | 3/2011 |
| JP | 2011-193306 | 9/2011 |
| WO | WO 2012067959 A2 * | 5/2012 ............ A61B 6/465 |

OTHER PUBLICATIONS

Töpfer, Karin, and John Dehority. "Optimized operation and offset corrections for a battery-powered wireless digital x-ray detector." In SPIE Medical Imaging, pp. 72583O-72583O. International Society for Optics and Photonics, 2009.*

(Continued)

Primary Examiner — Carol Wang

(57) ABSTRACT

A radiographic imaging system and digital detector detect extraneous signals during DR detector image readout and compensate or remove extraneous signal artifacts from radiographic images. Novel capture and post processing procedures prevent undesirable noise artifacts from appearing in final radiographic images.

19 Claims, 17 Drawing Sheets

(51) Int. Cl.
  *H04N 5/32* (2006.01)
  *H04N 5/359* (2011.01)
  *H04N 5/361* (2011.01)

(52) U.S. Cl.
  CPC .............. *G06T 5/002* (2013.01); *H04N 5/32* (2013.01); *H04N 5/3597* (2013.01); *H04N 5/361* (2013.01); *G06T 2207/10116* (2013.01); *G06T 2207/20182* (2013.01)

(58) Field of Classification Search
  CPC ..... A61B 6/542; A61B 6/5258; A61B 6/4233; A61B 6/5205
  See application file for complete search history.

(56) References Cited

U.S. PATENT DOCUMENTS

| | | | | |
|---|---|---|---|---|
| 5,923,722 A * | 7/1999 | Schulz | ............... | G01N 23/04 348/E5.088 |
| 6,101,287 A * | 8/2000 | Corum | ............... | G06T 5/50 348/E5.081 |
| 7,810,997 B2 * | 10/2010 | Okamura | ............... | A61B 6/00 378/207 |
| 2002/0085667 A1 * | 7/2002 | Miller | ............... | H04N 5/2176 378/48 |
| 2003/0072418 A1 * | 4/2003 | Albagli | ............... | A61B 6/583 378/207 |
| 2003/0083564 A1 * | 5/2003 | Ghelmansarai | ............... | A61B 6/00 600/407 |
| 2003/0223539 A1 * | 12/2003 | Granfors | ............... | H04N 5/361 378/98.8 |
| 2006/0227935 A1 * | 10/2006 | Ikeda | ............... | A61B 6/00 378/98.12 |
| 2006/0241372 A1 * | 10/2006 | Nekovar | ............... | G03B 42/021 600/407 |
| 2009/0080764 A1 * | 3/2009 | Srinivasan | ............... | G01N 23/04 382/150 |
| 2009/0129653 A1 * | 5/2009 | Dehority | ............... | A61B 6/4233 382/132 |
| 2010/0020933 A1 * | 1/2010 | Topfer | ............... | G06T 5/50 378/98.11 |
| 2012/0138808 A1 * | 6/2012 | Jung | ............... | G01T 1/247 250/370.09 |
| 2012/0189100 A1 * | 7/2012 | Liu | ............... | G01T 1/247 378/62 |
| 2012/0230469 A1 * | 9/2012 | Yamanaka | ............... | A61B 6/5205 378/62 |
| 2013/0028499 A1 * | 1/2013 | Tsujii | ............... | A61B 6/585 382/132 |
| 2013/0093912 A1 * | 4/2013 | Uchida | ............... | H04N 5/365 348/222.1 |
| 2015/0131777 A1 * | 5/2015 | Makifuchi | ............... | A61B 6/4291 378/36 |

OTHER PUBLICATIONS

International Search Report for International application No. PCT/US2014/064468, dated Feb. 17, 2015, 2 pages.

* cited by examiner

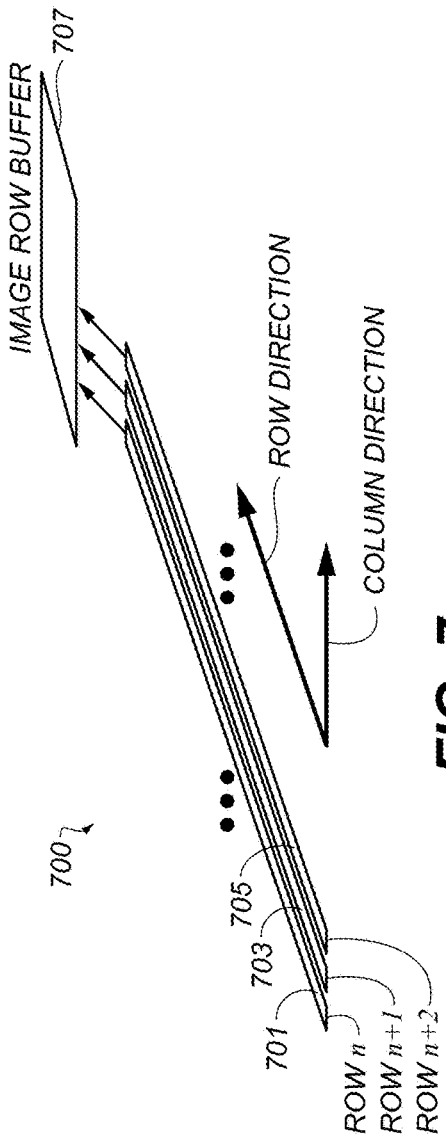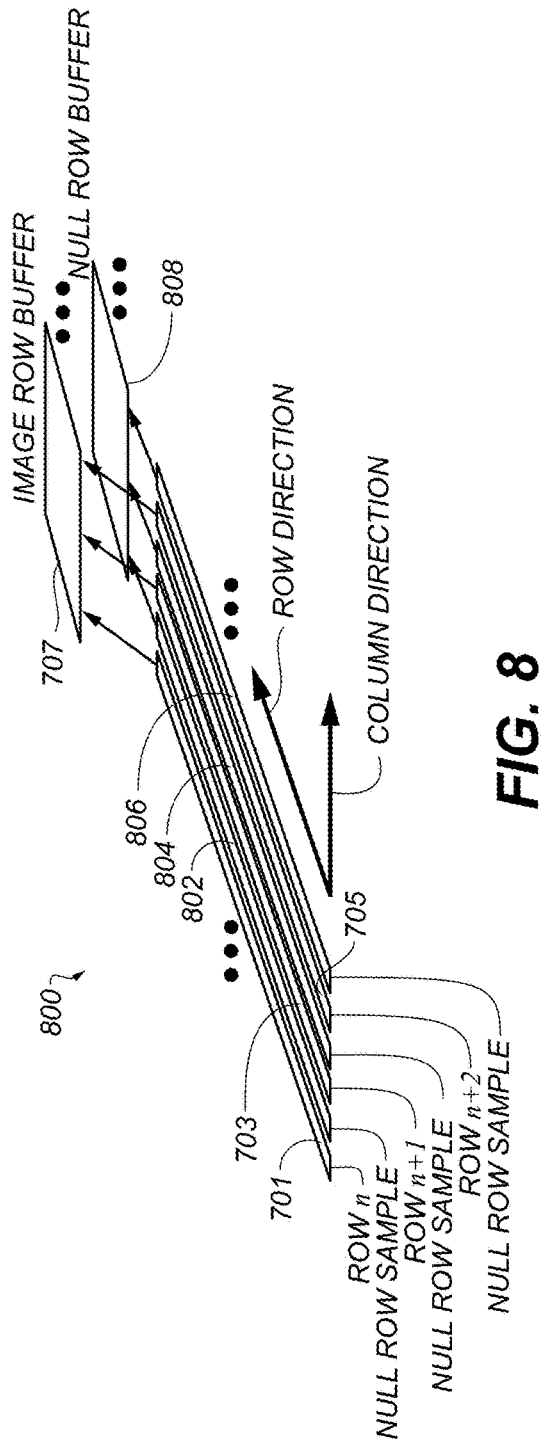

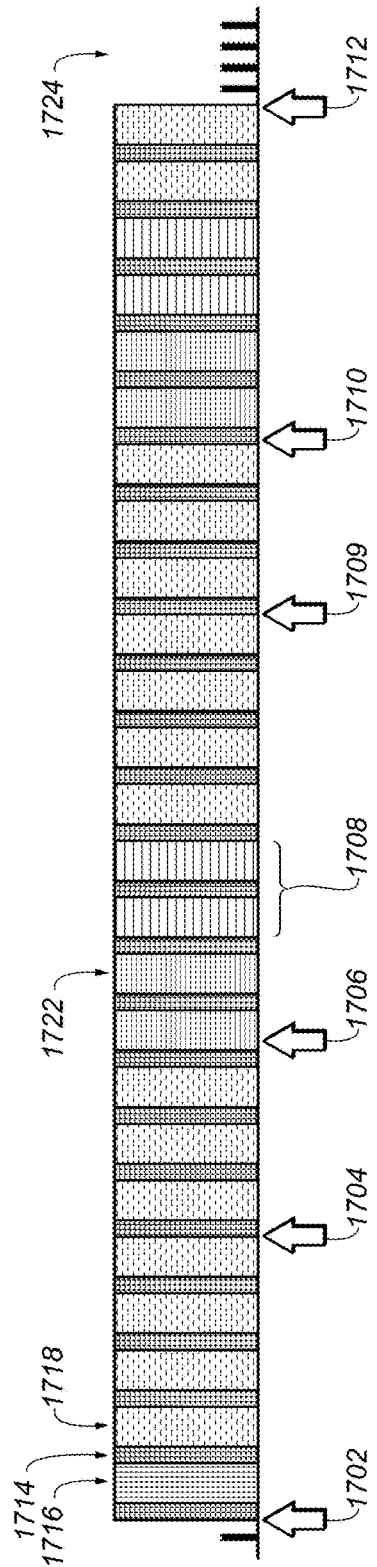
FIG. 17
FIG. 18A
FIG. 18B

DIGITAL RADIOGRAPHY DETECTOR IMAGE READOUT SYSTEM AND PROCESS

CROSS REFERENCE TO RELATED APPLICATIONS

This application claims priority to U.S. Patent Application Ser. No. 61/901,699, filed Nov. 8, 2013, in the names of Topfer et al., and entitled DR DETECTOR IMAGE READOUT PROCESS.

FIELD OF THE INVENTION

The invention relates generally to the field of medical imaging, and in particular to radiographic imaging, digital radiographic (DR) detectors, and more particularly to apparatus, systems, and/or methods for enhancing the signal integrity of the image readout operation of a DR detector.

BACKGROUND

Stationary and mobile radiographic imaging equipment is employed in medical facilities to capture x-ray images on an x-ray detector. Such medical x-ray images may be captured using various techniques such as computed radiography (CR) and digital radiography in radiography detectors.

A related art DR imaging panel acquires image data from a scintillating medium using an array of individual sensors, arranged in a row-by-column matrix, in which each sensor provides a single pixel of image data. Each pixel generally includes a photosensor and a switching element that may be fabricated in a co-planar or a vertically integrated manner, as is generally known in the art. In these imaging devices, hydrogenated amorphous silicon (a-Si:H) is commonly used to form the photodiode and the thin-film transistor switch needed for each pixel. In one known imaging arrangement, a frontplane includes an array of photosensitive elements, and a backplane includes an array of thin-film transistor (TFT) switches.

There is a need for improvements in the consistency and quality of medical x-ray images, particularly when obtained by an x-ray apparatus designed to operate with a-Si DR x-ray detectors. There is also a need for detection of an x-ray exposure event while avoiding invasive external hardware that imposes delays by linking to and holding off the x-ray generator control electronics until it determines that the DR detector system is ready for an x-ray exposure. Further, there is a need for detection of extraneous signals produced by low frequency magnetic fields present in image readout circuitry before an x-ray exposure and an imaging readout operation is initiated. It would be advantageous then to provide a method for the removal of image artifacts produced when the image readout process runs concurrently or overlaps with the x-ray beam exposure.

SUMMARY OF THE INVENTION

A radiographic imaging system and digital detector detect extraneous signals during DR detector image readout and compensate or remove extraneous signal artifacts from radiographic images. Novel capture and post processing procedures prevent undesirable noise artifacts from appearing in final radiographic images. An advantage that may be realized in the practice of some disclosed embodiments of the digital radiography detector image readout process is improved radiographic image quality.

In one embodiment, a method of image correction for a digital radiographic detector comprises obtaining a dark frame, obtaining a dark leakage frame, obtaining an image data frame, obtaining an exposure leakage frame, and obtaining an image lag data frame. The image data frame and the image lag data frame are dark corrected using the dark frame. The exposure leakage frame is dark corrected using the dark leakage frame. The dark corrected image lag data frame and the dark corrected exposure leakage frame are further corrected with a noise correction process. The noise corrected, dark corrected exposure leakage frame, the noise corrected, dark corrected image lag data frame, and the dark corrected image data frame are combined to obtain a corrected image frame.

In another embodiment, a method of image correction for a digital radiographic detector comprises obtaining a dark frame, obtaining a dark leakage frame, obtaining an image data frame, and obtaining an exposure leakage frame. The image data frame is dark corrected using the dark frame. The exposure leakage frame is dark corrected using the dark leakage frame. The dark corrected exposure leakage frame and the dark corrected image data frame are combined to obtain a corrected image frame.

In another embodiment, a method of image correction for a digital radiographic detector comprises obtaining a dark corrected image data frame, obtaining a dark corrected exposure leakage frame, and combining them to obtain a corrected image frame.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 7 is a diagram showing an exemplary readout process for an image readout operation in a DR detector.

FIG. 8 is a diagram showing an exemplary image readout process using an interleaved null row read process for a DR detector.

FIG. 17 illustrates exemplary DR detector integration and readout cycles.

FIGS. 18A-B illustrate illustrates image and null row read cycles.

DETAILED DESCRIPTION OF THE INVENTION

Figure 1:
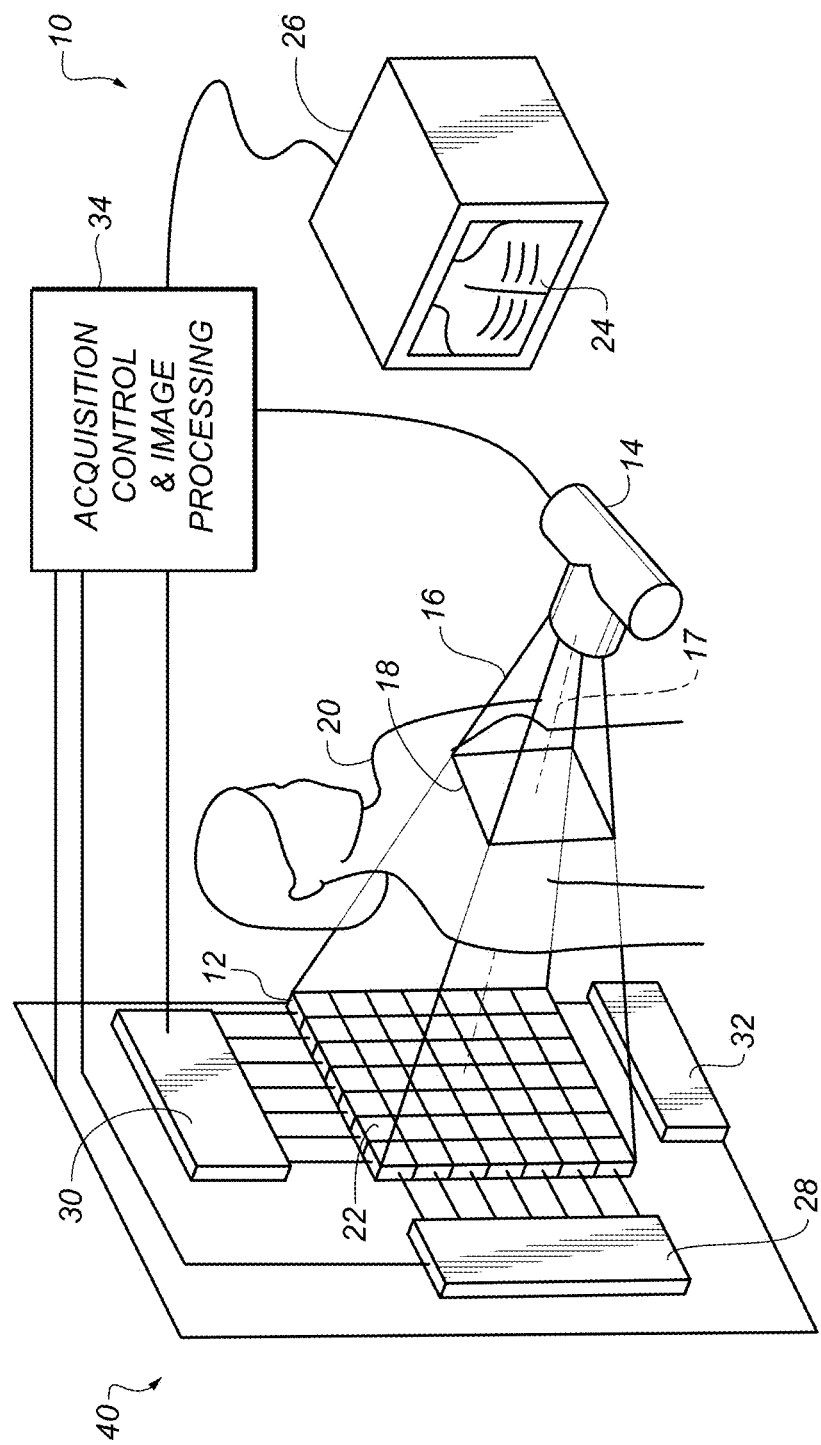
FIG. 1 is a perspective view of an exemplary radiographic imaging system.

During an imaging readout operation performed by a DR detector there may exist unwanted extraneous signals that affect the DR detector's readout operation by introducing data errors that result in degraded image quality when the image data is finally processed. The extraneous signals may originate from noise sources external to the detector or from sources within the detector housing. Extraneous signals may also be produced during the readout operation if the image readout occurs concurrently with an activation of the x-ray source. Extraneous magnetic fields may be generated by the DR system and related equipment in an imaging room which may cause parasitic effects in the readout circuitry or on the pixels in the photosensor array.

One type of external extraneous signal commonly found to interfere with DR detector image readout operations is caused by low frequency magnetic fields in the range of about one kilohertz up to hundreds of kilohertz. These magnetic fields may be produced by electrical equipment in close proximity to the DR detector. Typically, these noise inducing magnetic fields are generated by components such as inductors or AC motors that emit magnetic flux. Another source of extraneous noise includes power supplies that generate high voltages. These power supplies are often required by automatic exposure control hardware used with DR detectors.

Extraneous noise affecting operations of the DR detector find entry points into the DR detector via parasitic capacitance intrinsic to the pixel array of the DR detector. A DR detector's readout operation may be performed after an x-ray source has exposed the patient and detector to x-ray radiation for a fixed exposure period predetermined and configured by an operator. The corresponding DR detector integration period, which is concurrent with the x-ray source "on time", may be configured to terminate after the x-ray source is turned off, because the image readout process normally follows the DR detector integration period. A portion of an image readout process occurring during the x-ray source exposure period is susceptible to the noise signals caused by the x-ray source.

There may be occasions when it is desirable to perform the image readout concurrently with the x-ray exposure. In this case the image readout from the DR detector may be initiated before the x-ray source exposure process has begun. The image readout process may run continuously until all image frames are acquired and stored.

The start of an x-ray exposure may be detected by image processing software running concurrently with the readout process where the image processing software tests each read out image row for increased signal intensity. After the start of the x-ray beam exposure is detected, the row by row image readout continues until the signal level returns to a pre-exposure level at about zero. After the x-ray beam exposure period has finished, the image readout process continues for at least one more image readout cycle to obtain a final 'image free' frame (unexposed) of data called a dark image, or lag image, that is used to adjust and correct previous image data frames. When all collected image frames have been stored in an image buffer, which may include an image buffer internal to the DR detector comprising electronic memory locations for storing several image data frames, a post image processing function is performed on the buffered image frames to produce the final image. This method of image readout for a DR detector has the benefit of providing asynchronous image readout of an x-ray exposure event without the need for invasive external hardware connections linking to and holding off the x-ray source control electronics until the DR detector system is ready for an x-ray exposure. This image readout method, however, causes image artifacts induced in part by parasitic capacitance and x-ray beam exposure that generate leakage current during the readout method.

FIG. 1 is a perspective view of a digital radiographic (DR) imaging system 10 that includes a generally planar DR detector 40 (shown without a housing for clarity of description), an x-ray source 14 configured to generate radiographic energy (x-ray radiation), and a digital monitor 26 configured to display images captured by the DR detector 40, according to one embodiment. The DR detector 40 may include a two dimensional array 12 of detector cells 22 (photosensors), arranged in electronically addressable rows and columns. The DR detector 40 may be positioned to receive x-rays 16 passing through a subject 20 during a radiographic energy exposure, or radiographic energy pulse, emitted by the x-ray source 14. As shown in FIG. 1, the radiographic imaging system 10 may use an x-ray source 14 that emits collimated x-rays 16, e.g. an x-ray beam, selectively aimed at and passing through a preselected region 18 of the subject 20. The x-ray beam 16 may be attenuated by varying degrees along its plurality of rays according to the internal structure of the subject 20, which attenuated rays are detected by the array 12 of photosensitive detector cells 22. The planar DR detector 40 is positioned, as much as possible, in a perpendicular relation to a substantially central ray 17 of the plurality of rays 16 emitted by the x-ray source 14. The array 12 of individual photosensitive cells (pixels) 22 may be electronically read out (scanned) by their position according to column and row. As used herein, the terms "column" and "row" refer to the vertical and horizontal arrangement of the photosensor cells 22 and, for clarity of description, it will be assumed that the rows extend horizontally and the columns extend vertically. However, the orientation of the columns and rows is arbitrary and does not limit the scope of any embodiments disclosed herein. Furthermore, the term "subject" may be illustrated as a human patient in the description of FIG. 1, however, a subject of a DR imaging system, as the term is used herein, may be a human, an animal, an inanimate object, or a portion thereof.

In one exemplary embodiment, the rows of photosensitive cells 22 may be scanned one or more at a time by electronic scanning circuit 28 so that the exposure data from the array 12 may be transmitted to electronic read-out circuit 30. Each photosensitive cell 22 may independently store a charge proportional to an intensity, or energy level, of the attenuated radiographic radiation, or x-rays, received and absorbed in the cell. Thus, each photosensitive cell, when read-out, provides information defining a pixel of a radiographic image 24, e.g. a brightness level or an amount of energy absorbed by the pixel, that may be digitally decoded by image processing electronics 34 and transmitted to be displayed by the digital monitor 26 for viewing by a user. An electronic bias circuit 32 is electrically connected to the two-dimensional detector array 12 to provide a bias voltage to each of the photosensitive cells 22.

Each of the bias circuit 32, the scanning circuit 28, and the read-out circuit 30, may communicate with an acquisition control and image processing unit 34 over a connected cable (wired), or the DR detector may be equipped with a wireless transmitter to transmit radiographic image data wirelessly to the acquisition control and image processing unit 34. The acquisition control and image processing unit 34 may include a processor and electronic memory (not shown) to control operations of the DR detector 40 as described herein, including control of circuits 28, 30, and 32, for example, by use of programmed instructions. The acquisition control and image processing unit 34 may also be used to control activation of the x-ray source 14 during a radiographic exposure, controlling an x-ray tube electric current magnitude, and thus the fluence of x-rays in x-ray beam 16, and the x-ray tube voltage, and thus the energy level of the x-rays in x-ray beam 16.

The acquisition control and image processing unit 34 may store a plurality of data frames received from the DR detector and transmit image (pixel) data to the monitor 26, based on the radiographic exposure data received from the array 12 of photosensitive cells 22 in the DR detector 40. Alternatively, acquisition control and image processing unit 34 may process the image data and store it, or it may store raw unprocessed image data, in local or remotely accessible memory.

With regard to a direct detection embodiment of DR detector 40, the photosensitive cells 22 may each include a sensing element sensitive to x-rays, i.e. it absorbs x-rays and generates an amount of charge carriers in proportion to a magnitude of the absorbed x-ray energy. A switching element may be configured to be selectively activated to read out the charge level of a corresponding x-ray sensing element. With regard to an indirect detection embodiment of DR detector 40, photosensitive cells 22 may each include a sensing element sensitive to light rays in the visible spectrum, i.e. it absorbs light rays and generates an amount of charge carriers in proportion to a magnitude of the absorbed light energy, and a switching element that is selectively activated to read the charge level of the corresponding sensing element. A scintillator, or wavelength converter, is disposed over the light sensitive sensing elements to convert incident x-ray radiographic energy to visible light energy. Thus, in the embodiments disclosed herein, it should be noted that the DR detector 40 may include an indirect or direct type of DR detector.

Examples of sensing elements used in sensing array 12 include various types of photoelectric conversion devices (e.g., photosensors) such as photodiodes (P-N or PIN diodes), photo-capacitors (MIS), photo-transistors or photoconductors. Examples of switching elements used for signal read-out include MOS transistors, bipolar transistors and other p-n junction components.

Figure 2:
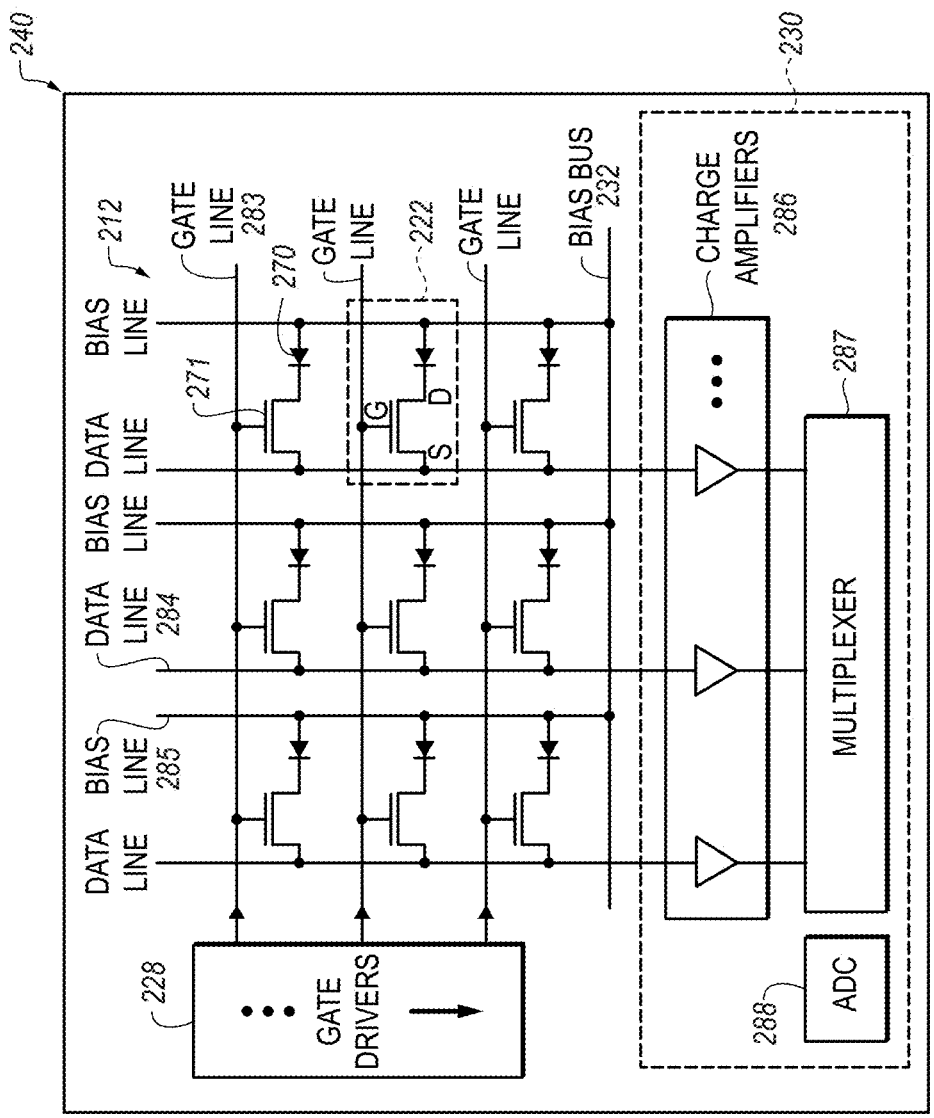
FIG. 2 is a schematic diagram of a portion of an exemplary imaging array for a DR detector used in the exemplary radiographic imaging system of FIG. 1.

FIG. 2 is a schematic diagram 240 of a portion of a two-dimensional array 12 for the DR detector 40. The array of photosensor cells 212, whose operation may be consistent with the photosensor array 12 described above, may include a number of hydrogenated amorphous silicon (a-Si:H) n-i-p photodiodes 270 and thin film transistors (TFTs) 271 formed as field effect transistors (FETs) each having gate (G), source (S), and drain (D) terminals. In embodiments of DR detector 40 disclosed herein, such as a multilayer DR detector, the two-dimensional array of photosensor cells 12 may be formed in a device layer that abuts adjacent layers of the DR detector structure. A plurality of gate driver circuits 228 may be electrically connected to a plurality of gate lines 283 which control a voltage applied to the gates of TFTs 271, a plurality of readout circuits 230 may be electrically connected to data lines 284, and a plurality of bias lines 285 may be electrically connected to a bias line bus or a variable bias reference voltage line 232 which controls a voltage applied to the photodiodes 270. Charge amplifiers 286 may be electrically connected to the data lines 284 to receive signals therefrom. Outputs from the charge amplifiers 286 may be electrically connected to a multiplexer 287, such as an analog multiplexer, then to an analog-to-digital converter (ADC) 288, or they may be directly connected to the ADC, to stream out the digital radiographic image data at desired rates. In one embodiment, the schematic diagram of FIG. 2 may represent a portion of a DR detector 40 such as an a-Si:H based indirect flat panel imager.

Incident x-rays, or x-ray photons, 16 are converted to optical photons, or light rays, by a scintillator, which light rays are subsequently converted to electron-hole pairs, or charges, upon impacting the a-Si:H n-i-p photodiodes 270. In one embodiment, an exemplary detector cell 222, which may be equivalently referred to herein as a pixel, may include a photodiode 270 having its anode electrically connected to a bias line 285 and its cathode electrically connected to the drain (D) of TFT 271. The bias reference voltage line 232 may control a bias voltage of the photodiodes 270 at each of the detector cells 222. The charge capacity of each of the photodiodes 270 is a function of its bias voltage and its capacitance. In general, a reverse bias voltage, e.g. a negative voltage, may be applied to the bias lines 285 to create an electric field (and hence a depletion region) across the p-n junction of each of the photodiodes 270 to enhance its collection efficiency for the charges generated by incident light rays. The image signal represented by the array of photosensor cells 212 may be integrated by the photodiodes while their associated TFTs 271 are held in a non-conducting (off) state, for example, by maintaining the gate lines 283 at a negative voltage via the gate driver circuits 228. The photosensor cell array 212 may be read out by sequentially switching rows of the TFTs 271 to a conducting (on) state by means of the gate driver circuits 228. When a row of the pixels 22 is switched to a conducting state, for example by applying a positive voltage to the corresponding gate line 283, collected charge from the photodiode in those pixels may be transferred along data lines 284 and integrated by the external charge amplifier circuits 286. The row may then be switched back to a non-conducting state, and the process is repeated for each row until the entire array of photosensor cells 212 has been read out. The integrated signal outputs are transferred from the external charge amplifiers 286 to an analog-to-digital converter (ADC) 288 using a parallel-to-serial converter, such as multiplexer 287, which together comprise read-out circuit 230.

This digital image information may be subsequently processed by image processing system 34 to yield a digital image which may then be digitally stored and immediately displayed on monitor 26, or it may be displayed at a later time by accessing the digital electronic memory containing the stored image. The flat panel DR detector 40 having an imaging array as described with reference to FIG. 2 is capable of both single-shot (e.g., static, radiographic) and continuous (e.g., fluoroscopic) image acquisition.

Figure 3:
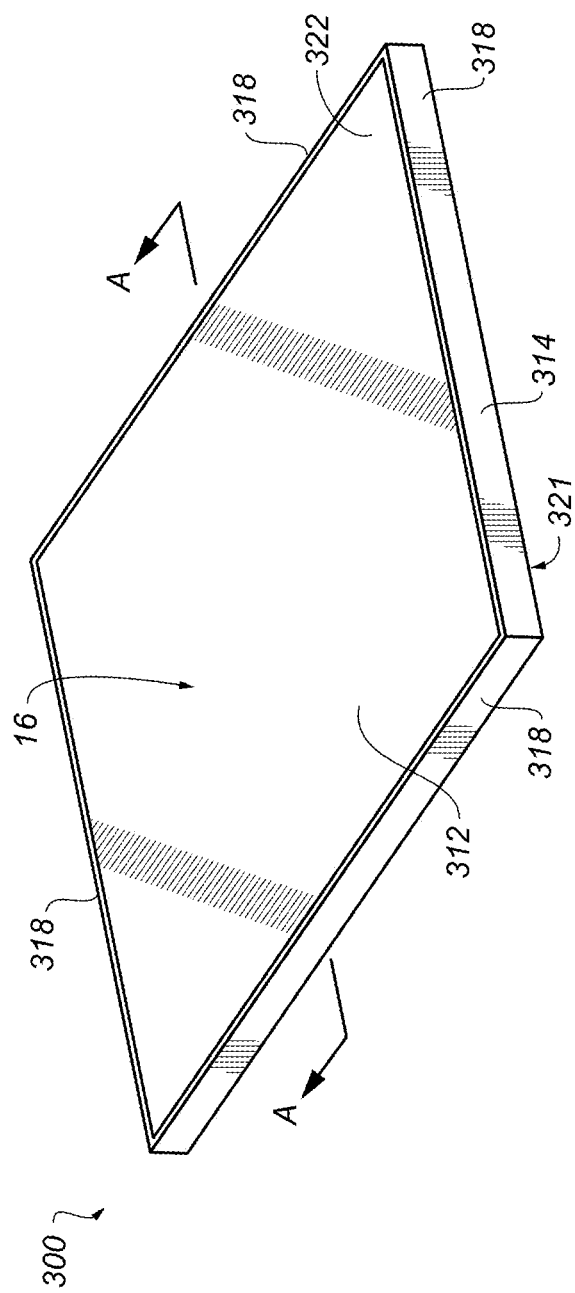
FIG. 3 shows a perspective view of an exemplary portable wireless DR detector.

FIG. 3 shows a perspective view of an exemplary prior art generally rectangular, planar, portable wireless DR detector 300 according to an embodiment of DR detector 40 disclosed herein. The DR detector 300 may include a housing 314 that encloses a multilayer structure comprising the photosensor array portion 22 of the DR detector 300. The housing 314 of the DR detector 300 may include a continuous, rigid, radio-opaque enclosure surrounding an interior volume of the DR detector 300. The housing 314 may comprise four orthogonal edges 318 and a bottom side 321 disposed opposite a top side 322 of the DR detector 300. A top cover 312 encloses the top side 322 which, together with the housing 314 substantially encloses the multilayer structure in the interior volume of the DR detector 300, and may be attached to the housing 314 to form a seal therebetween. The top cover 312 may be made of a material that passes x-rays 16 without significant attenuation thereof, i.e., a radiolucent material, such as a carbon fiber or plastic material.

Figure 4:
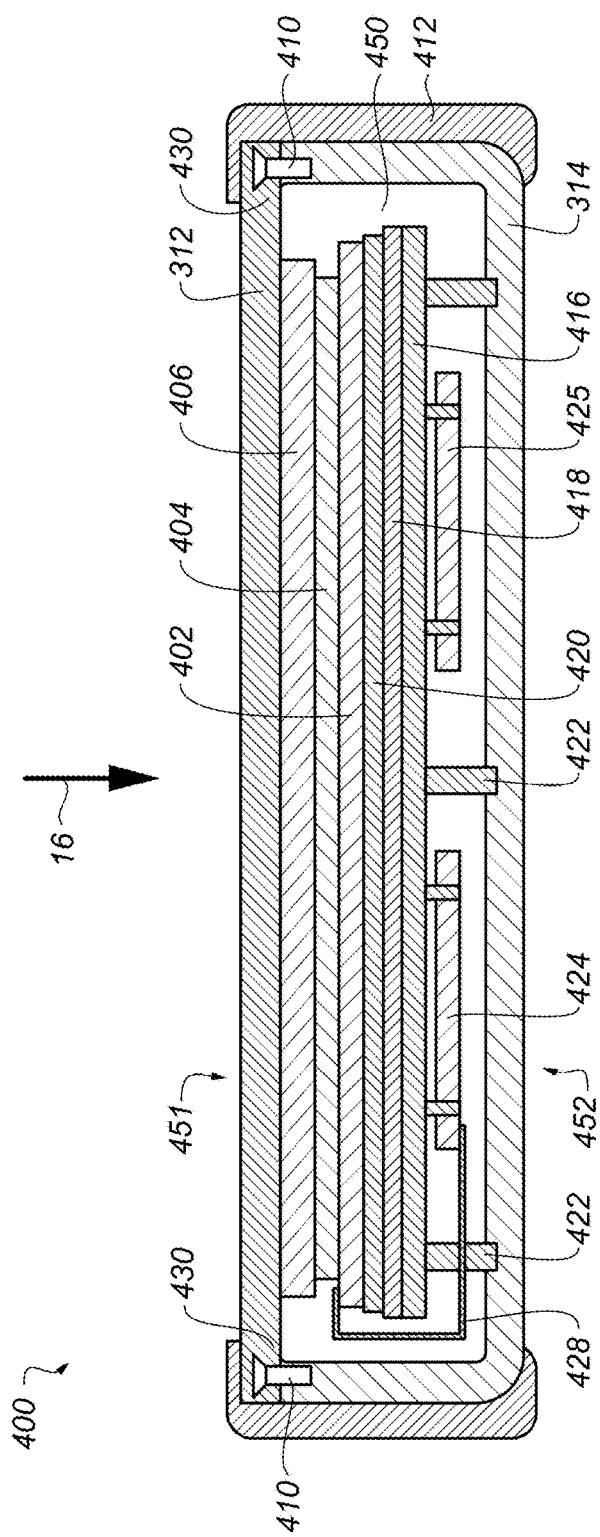
FIG. 4 is an exemplary cross-sectional view along section line A-A of the portable wireless DR detector of FIG. 3.

With reference to FIG. 4, there is illustrated in schematic form an exemplary cross-section view along section A-A of the exemplary embodiment of the DR detector 300 (FIG. 3). For spatial reference purposes, one major surface of the DR detector 400 may be referred to as the top side 451 and a second major surface may be referred to as the bottom side 452, as used herein. The multilayer imaging structure is disposed within the interior volume 450 enclosed by the housing 314 and top cover 312 and may include a scintillator layer 404 over the two-dimensional imaging sensor array 12 shown schematically as the device layer 402. The scintillator layer 404 may be directly under (e.g., directly connected to) the radiolucent top cover 312, and the imaging array 402 may be directly under the scintillator 404. Alternatively, a flexible layer 406 may be positioned between the scintillator layer 404 and the top cover 312 as part of the multilayer structure to provide shock absorption. The flexible layer 406 may be selected to provide an amount of flexible support for both the top cover 312 and the scintillator 404, and may comprise a foam rubber type of material.

A substrate layer 420 may be disposed under the imaging array 402, such as a rigid glass layer upon which the array of photosensors 402 is formed, and may comprise another layer of the multilayer structure. Under the substrate layer 420 a radio-opaque shield layer 418 may be used as an x-ray blocking layer to help prevent scattering of x-rays passing through the substrate layer 420 as well as to block x-rays reflected from other surfaces in the interior volume 450. Readout electronics, including the scanning circuit 28, the read-out circuit 30, and the bias circuit 32 (FIG. 1) may be formed co-planar with the imaging array 402 or, as shown, may be disposed below frame support member 416 in the form of integrated circuits electrically connected to printed circuit boards 424, 425. The frame support member 416 is fixed to the housing 314 using frame support beams 422 to provide support for the multilayer structure just described. The imaging array 402 is electrically connected to the readout electronics, 28, 30, 32, over a flexible connector 428 which may comprise a plurality of flexible, sealed conductors. X-ray flux may pass through the radiolucent top panel cover 312, in the direction represented by an exemplary x-ray beam 16, and impinge upon scintillator 404 where stimulation by the high-energy x-rays 16, or photons, causes the scintillator 404 to emit lower energy photons as visible light rays which are then received in the photosensors of imaging array 402. The frame support member 416 may securely mount the multilayer structure to the housing 314 and may further operate as a shock absorber by disposing elastic pads (not shown) between the frame support beams 422 and the housing 314. Fasteners 410, such as screws, may be used to fixedly attach the top cover 312 to the housing 314 and create a seal therebetween in the region 430 where they come into contact. In one embodiment, an external bumper 412 may be attached along the edges 318 of the DR detector 400 to provide additional shock-absorption.

Figure 5:
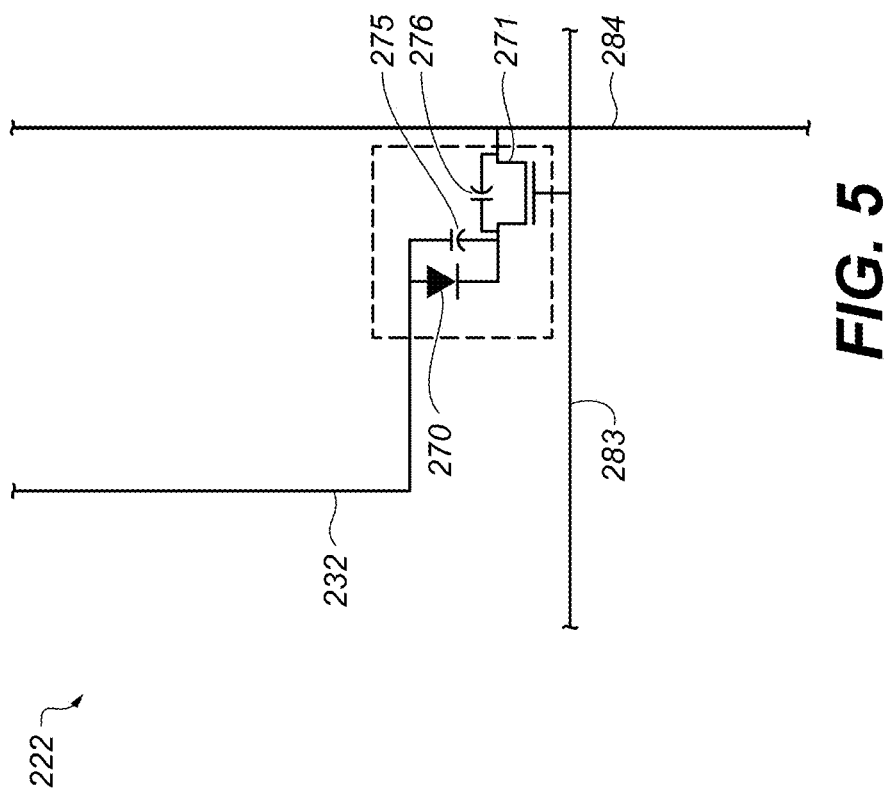
FIG. 5 is a diagram showing an exemplary pixel cell and selected constituent components.

FIG. 5 illustrates pixel cell 222 connected to bias bus 232, gate line 283, and data line 284, including a representation of a parasitic capacitance 276 between the source and drain of TFT 271. The parasitic capacitance 276 couples the cathode of photodiode 270 to data line 284. The parasitic capacitance introduces a noise signal into the data line 284 during an image readout operation by creating a low impedance path around TFT 271 even when the TFT 271 is in a high impedance 'OFF' state. The charge storage capability of the photodiode 270 is represented by the capacitance 275.

Figure 6B:
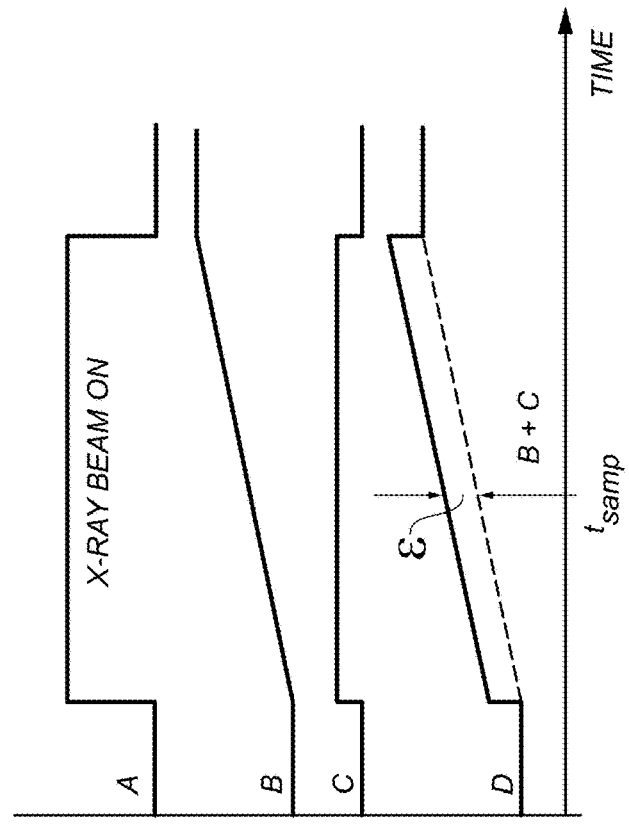
FIGS. 6A-B illustrate an exemplary pixel cell showing the generation of extraneous signals.
Figure 6A:
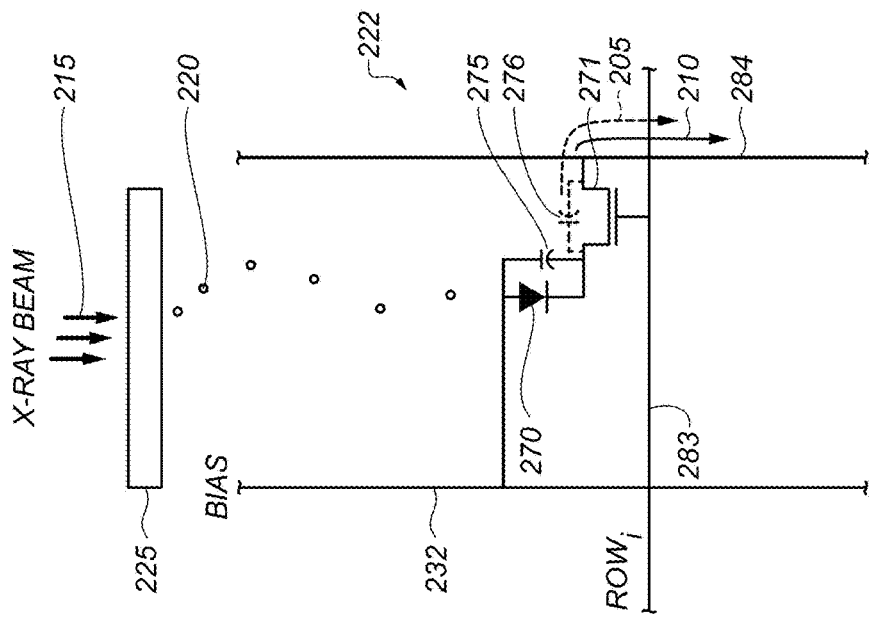

FIG. 6A illustrate an exemplary deleterious process occurring in the pixel cell 222 caused by effects of the extraneous signals. FIG. 6A includes two representative signal paths from photodiode 270. Signal path 210 is connected from the cathode of photodiode 270 through TFT 271 and out to data line 284 toward downstream read out circuitry, and is designed to carry DR detector image signals. The second signal path 205 is a parasitic signal path that bypasses TFT 271 via a parasitic capacitance 276 which effectively couples the drain and source of the TFT 271. This first signal path 210 is created when TFT 271 is switched to the low impedance 'ON' state using a signal on the gate line 283 delivered by a gate driver connected to the gate line 283. This first signal path 210 is the designed signal conduction path and is used during an image readout operation to read out the charge level stored in the photodiode 270 via its capacitive property, represented by capacitance 275. The parasitic capacitance 276 may be referred to as a leakage capacitance that creates a low impedance conductive path for time varying (non-DC) signals. An x-ray exposure period causes such a time varying signal due to the integration time wherein charge accumulates in the photodiode via a photon generated photodiode current, and so causes leakage into the data line 284 across the parasitic capacitance 276. An exemplary x-ray beam (photons) 215 may be received at the DR pixel 22, initially impacting a scintillator layer 225 which, in response to the x-ray photons, emits light photons 220. Light photons 220, in turn, impact photodiode 270 which, in response, generates charge carriers which are accumulated in the photodiode due to its intrinsic capacitance 275.

The graph of FIG. 6B illustrates a plot of various waveforms on its vertical axis versus time, on its horizontal axis. Waveform A represents an x-ray pulse of finite duration received by the pixel 222. While the x-ray pulse impacts the pixel 222, charge carriers accumulate in the photodiode 270 which is represented as a voltage ramp-up in waveform B. The voltage ramp B may be represented as a time-varying voltage (dv/dt) and so causes a leakage across the parasitic capacitance 276, represented by the leakage current waveform C, through the leakage path 205 as described above. Thus, the total signal as measured on data line 284, represented by total signal waveform D, during an x-ray pulse includes the sum of the pixel voltage (waveform B) plus the erroneous and extraneous leakage current of waveform C. As shown in the total signal waveform D at time $t_{samp}$, an error ε is caused by the leakage current. The time varying voltage produces leakage current over signal path 205 even when TFT 271 is in the high impedance 'OFF' state. This leakage current is the source of the extraneous data line signal caused by an x-ray exposure performed concurrently with an image readout operation.

During image readout of any pixel, an extraneous leakage current signal will be present on the data line and will equal the summed total of all other leakage currents in the pixels connected to the same data line, i.e. a column of pixels, by their parasitic capacitance 276. This results in an image readout error that is present only during the time that the pixel photosensor array receives x-ray fluence during an x-ray exposure. Image readout and x-ray exposure duration will rarely be equivalent, therefore, to insure that the image readout operation acquires all image data (photosensor charge), the image readout operation may be configured to extend longer in time than the x-ray exposure. This configuration will result in a part, but not all, of the image readout time duration to be affected by the extraneous leakage current.

FIG. 7 illustrates one embodiment of an image readout process 700 wherein rows of exemplary pixels n 701, n+1 702, n+2 703, and so on, are each read out one at a time in sequence and stored into the image row buffer 707. FIG. 8 illustrates an embodiment of a modified image readout process 800 using null row samples 802, 804, 806, in a readout process to acquire complementary data sets that include image data information from image readouts 701, 703, 705 stored in image buffer 707, and extraneous signal data information from null row readouts 802, 804, 806, stored in null row buffer 808. The buffers 707, 808, may include electronic memory for storing a plurality of image data frames in different addressable portions of the memory. Referring to FIG. 7 and FIG. 8, one modified image readout process embodiment may include successive image row 701, 703, 705, readouts that are interleaved with null row 802, 804, 806, readouts. Starting with read out of a particular image row n 701, the image data is digitized by A/D converters 288 (FIG. 2) and stored into the image row buffer 707 at a memory location corresponding to image row n 701. This image row readout is immediately followed by a null row 802 readout wherein the gate line 283 (FIG. 2) for that particular row of TFTs are turned off and any extraneous signal induced onto their corresponding data lines is digitized by A/D converters 288 and then stored into a null row buffer 808 at a memory location corresponding to image row n 701 of the image data. This interleaved process of alternate image row 701, 702, 705, readouts each followed by a null row 802, 804, 806, readout, respectively, may be termed a null row read operation and may be used to detect and capture extraneous signals present on the data lines 284. As described herein, such an interleaved process may be further modified to include two or more null row reads after each image data read, rather than only one null row read. Thus, each row signal can be read out (with gate line "on") followed by two null row readout cycles (with gate line "off") for each row in the detector image frame.

A null row read operation is similar to the standard image row readout process except that during the null row read operation none of TFTs 271 of data lines 284 are set to the 'ON' state. For example, the null row read state may be achieved by keeping all row gate drivers 228 turned off while repeating the standard image row readout process. When a null row read process is performed the signal information acquired does not contain image information from the pixels' photodiodes 270 but rather may contain extraneous leakage signal information present on individual data lines 284.

Figure 9:
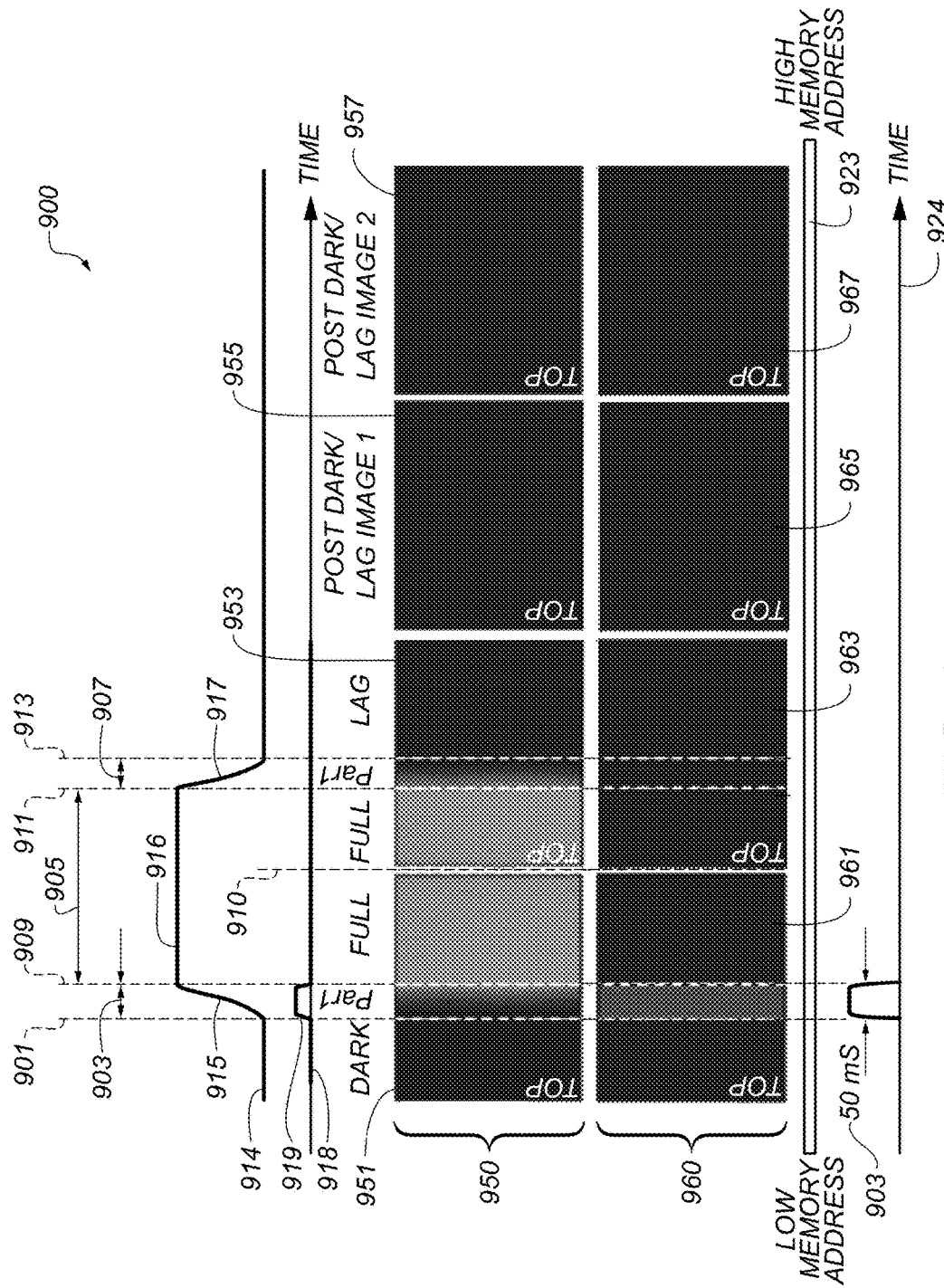
FIG. 9 is a diagram showing exemplary waveforms and image sets produced by an exemplary image readout procedure.

FIG. 9 illustrates a process 900 implementing complementary sets of image data frames 950, which set may include image data frames 951, 953, 955, and 957, and null row data frames 960, which set may include null row data frames 961, 963, 965, and 967. Each set, 950, 960, of data frames may include dark (or lag) image frames 955, 957, and dark (or lag) null row frames 965, 967, all data frames being acquired by performing the interleaved readout procedure as described herein with respect to FIG. 8. All the illustrated data frames 950, 960, may be stored in a storage buffer 923 comprising both the image row buffer 707 and null row buffer 808. With respect to a horizontal axis representing a time duration 924, the storage buffer 923 may include additional data frames captured during a time interval preceding a capture of the image and null row data frames 951, 961, respectively, and after a capture of the image and null row data frames, 957, 967, respectively. Thus, a null row data frame captured in a preceding time interval may include a band of extraneous signals such as illustrated in the null row data frame 961, which may be used to infer that extraneous magnetic flux is affecting operation of the DR detector. Such detection may be used to trigger a notification signal to the operator of the DR equipment to investigate potential sources of magnetic flux near the DR detector and to move such sources further from the DR equipment. As used herein, the term "frame" or "data frame" represents the data captured by the pixel array 212 in a DR detector 40.

Rows of pixel data are oriented vertically in the perspective of FIG. 9, wherein the first row of pixel data is located to the left of each data frame, 951-957 and 961-967, labeled "TOP", and the last row of pixel data (i.e. bottom) is located at the rightmost end of each data frame, 951-957 and 961-967, in the perspective of FIG. 9. The rows of pixels in the DR detector are repeatedly read out from top to bottom to generate the data frames 951-957 and 961-967 as shown.

An x-ray source activation is illustrated as an exemplary 50 ms exposure 903 beginning at a first point in time 901 and continuing until the x-ray source is deactivated, or turned off, at a second point in time 909. The amount of image data available to be read out from the pixel array 212 is represented by the graph 914. Points on the graph 914 correspond to rows of pixels being read out from a DR detector providing the image data frames 950-960. The graph 914 indicates that, during the 50 ms exposure 903, an amount of image data available in x-ray exposed pixels increases from about a zero percentage level at the activation time point 901 to about a full 100% level 916 at the deactivation time point 909, as indicated by the rising portion 915 of the graph 914. Because a number of rows of image data are being read out during the rise time 915, each such row will have been read out without complete image data. Those rows being read out closer in time to the x-ray source activation point 901 will contain a smaller percentage of the full image data than the rows being read out closer in time to the x-ray source deactivation point 909. Those rows being read out during the time duration 905, after the x-ray source deactivation point 909, will contain a full 100% of the image data as indicated by the horizontal portion 916 of the graph 914. Note that during this full readout period 905 the last row of the DR detector's pixel array will have been read out, at about the time 910, to complete the data frames 951, 961, and that the DR detector readout will repeat, after about the time 910, starting at the DR detector's first row (TOP) to generate the next data frames 953, 963 (and repeating the readout for successive dark frames 955-957 and 965-967 as illustrated).

The falling portion 917 of the graph 914 represents an amount of data in corresponding rows of pixels that have not yet been read out. This may be understood by noting that the row of pixels being read out from the DR detector corresponding to the point in time at about 901 is the same row of pixels being read out from the DR detector at the point in time at about 911 and the row of pixels being read out from the DR detector corresponding to the point in time at about 909 is the same row of pixels being read out from the DR detector at the point in time at about 913. Thus, the rows of pixels that were read out during the time period 903 contained partial image frame data (i.e., less than 100% due to the active x-ray exposure not having been completed) wherein the remaining unread portion of image frame data from those rows of pixels is read out during the time period 907. It may be noted that adding together the read out data from the rising and falling data portions 915, 917, respectively, results in a full 100% read out of available image data with respect to that portion (or rows) of the image data frame.

Activation of the x-ray source during the time period 903 causes an increase in charge carriers in each exposed pixel 222 of the imaging array 212, which results in an induced time varying voltage in each exposed pixel 222. As described herein, the time varying voltage (dv/dt) generates a parasitic signal 919, in the graph 918, in the pixels of the imaging array even when the readout TFTs 271 are not turned on. This parasitic effect is shown in the null row data buffer image 961 wherein extraneous signals are generated during the rising portion 915 of the graph 914 corresponding to the x-ray source activation time 903.

A complete DR image may be obtained from the DR detector data frames obtained thus far by first adding together the image data frames 951 and 953 which results in a 100% full read of the image frame data corresponding to an x-ray exposure 903, and then subtracting from that total the null row image data represented in the null row data frame 961. This combined image frame data may be comparable to the representation of the total data representing an x-ray exposure as described with reference to graph D of FIG. 6B, and the null row data frame may be comparable to the error data E as shown in FIG. 6B. Subtraction of the error data (null row data frame 961) results in a more accurate DR image.

Figure 11:
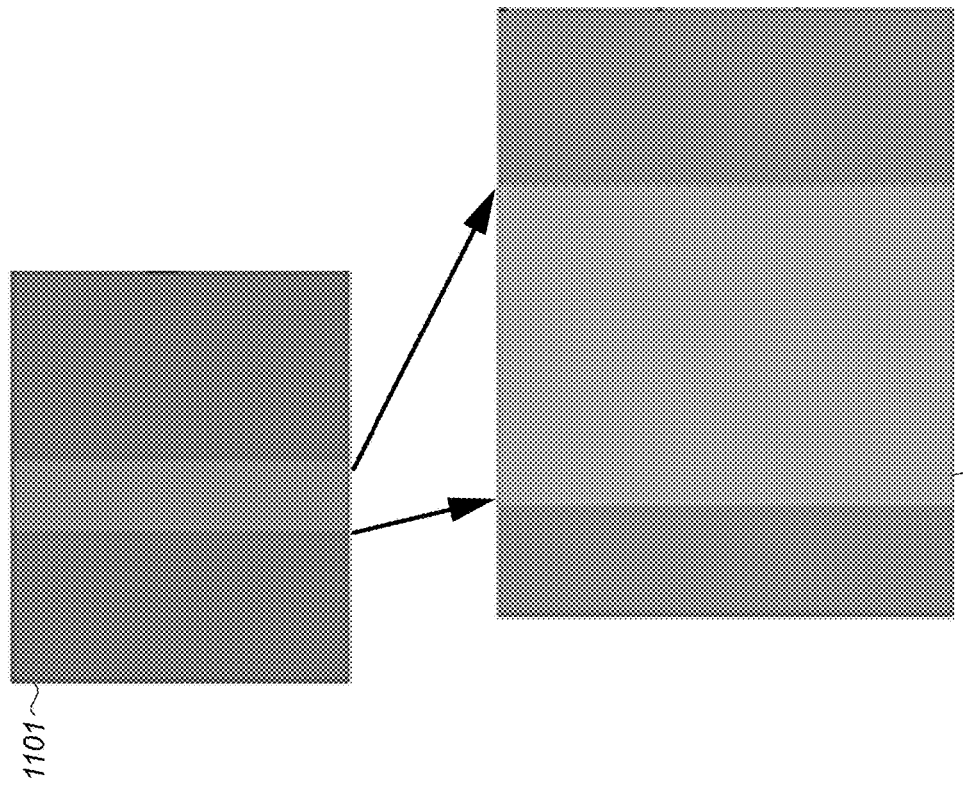
FIGS. 10-11 illustrate an exemplary reconstruction using two image data sets.
Figure 10:
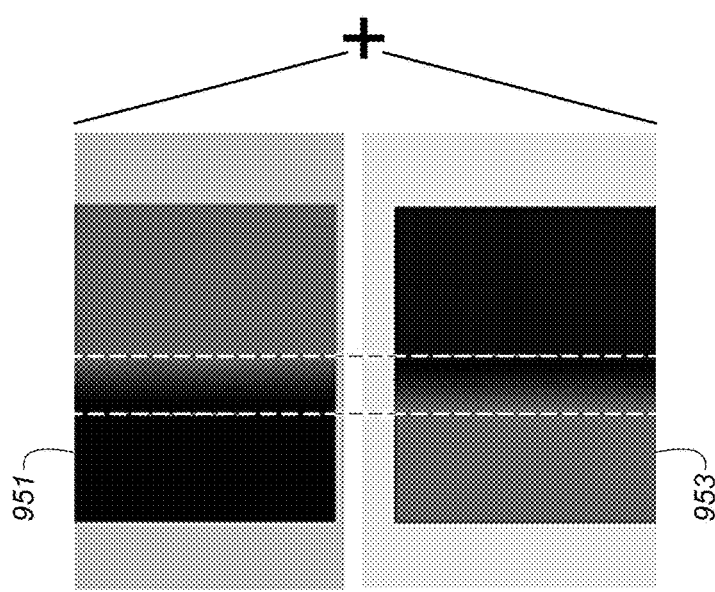

Referring now to FIGS. 10-11 there is illustrated an exemplary process of adding two image frames together as just described. Rows of pixel data are oriented vertically in the perspective of FIGS. 10-11. Image data frame 951 is added to image data frame 953 to obtain a total image data frame 1101 for the x-ray exposure 903 which reconstructs all the image data collected and stored in the image buffer. The various image frames 951, 953, 961, may be stored in separate portions of the image buffer 923, and may be combined by addition or subtraction to replace in the buffer memory one of the combined images or, alternatively, the combined image may be stored in another portion of the image buffer. The extraneous noise artifact may not be visible in the combined image of 1101 but can be better observed in the magnified image wherein the parasitic signal can be seen in the segment 1103 of the magnified combined image. This is the portion of the total image data that is corrected via subtraction of the null row read data.

Figure 12:
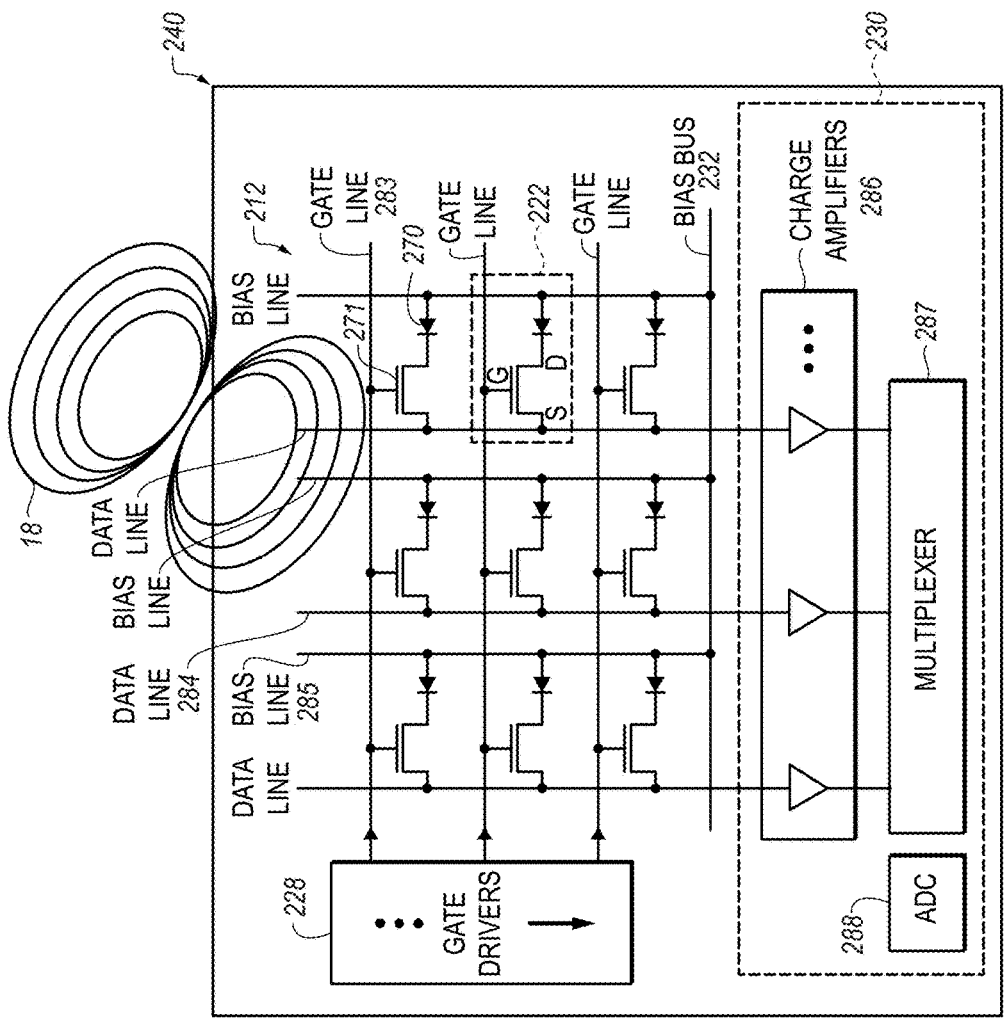
FIG. 12 is a diagram showing an exemplary pixel array sensor with row addressing and column readout components when subjected to an external low frequency magnetic field according to embodiments of the application.

FIG. 12 is another illustration showing the detector pixel sensor array 240 with an external magnetic field 18 in close proximity. As shown in the figure, the external flux from magnetic field 18 enters the DR detector enclosure 314 and links the internal data lines 284 of the pixel sensor array. If external magnetic field 18 is time varying, that is, has a frequency content that ranges from one kilohertz up to hundreds of kilohertz this can induce extraneous voltage signals onto the internal data lines. If present during a standard image readout process, the extraneous signals from this field will be added to the actual image data information produced by the x-ray exposure of the patient. This additional extraneous signal can introduce unacceptable image artifacts that degrade the final radiographic image.

With respect to embodiments disclosed herein, the additional signal contributed to the image signals by parasitic capacitances can be estimated by reading out every row twice: first the image information can be read out with the gate line on, followed by a second readout of the same row with the gate line off (null image or leakage image). In one embodiment, the null image can include the additional signal associated with the beam-on condition. To form reconstructed images of high quality, certain exemplary embodiments disclosed herein may combine at least two images with X-ray content, one null image and one or more lag frames. However, each additional frame contributes electronic noise, so that the resulting combined image has higher noise than a single regular radiographic capture. This can be particularly important for low exposures to the detector, where electronic noise can be the dominant factor relative to quantum noise from the X-ray exposures.

Figure 13:
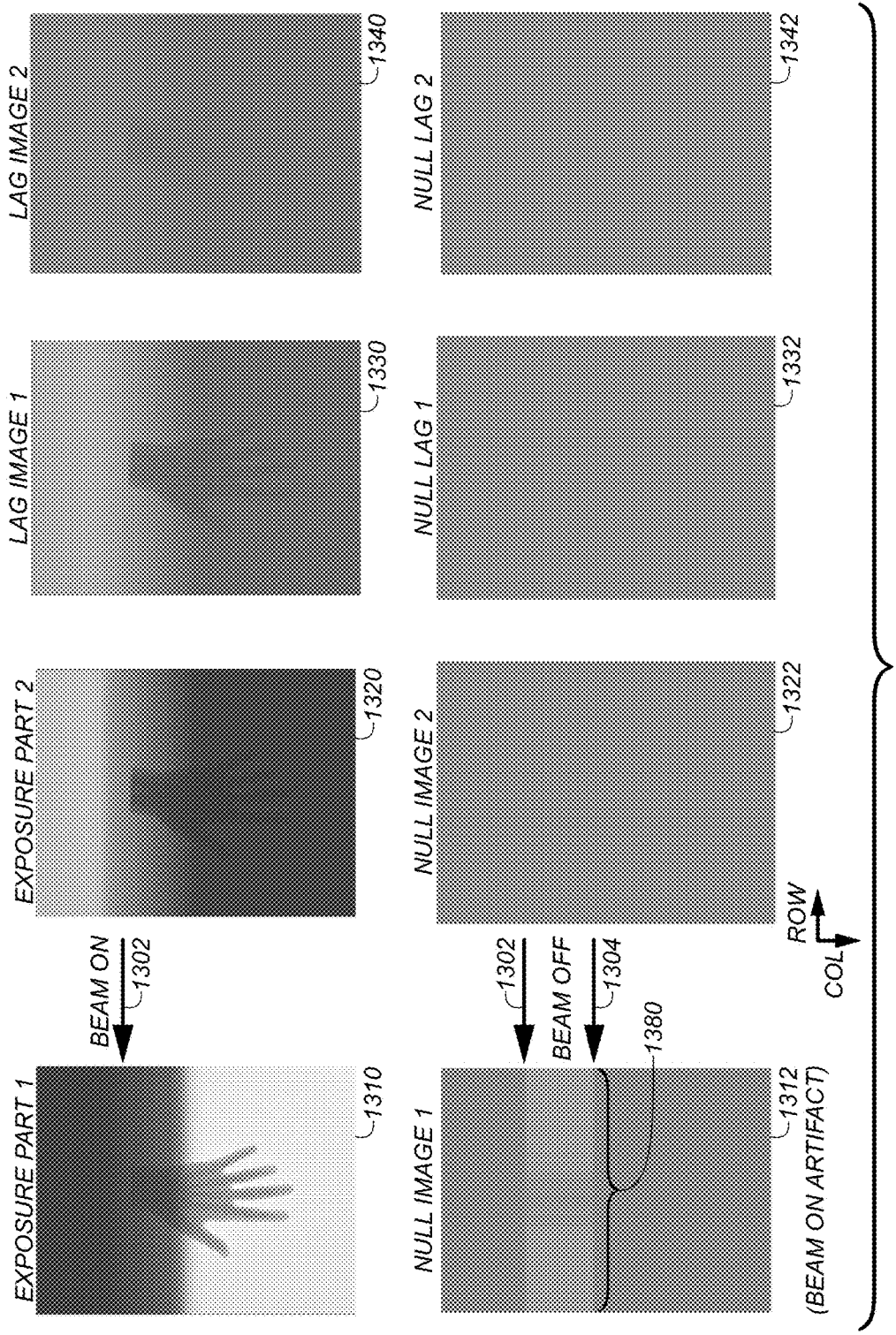
FIG. 13 is a diagram that shows exemplary images that can be used to restore the image information, decomposed into X-ray images and null images according to an embodiment of the application.

FIG. 13 is a diagram that shows exemplary images that can be used to restore the image information, decomposed into X-ray images and null images according to one embodiment. Rows of pixel data are oriented horizontally in the perspective of FIG. 13. All the images shown in FIG. 13 are dark-corrected using an average (e.g., 2, 4) of pre-dark frames (not shown). In one embodiment, the images are read out row by row (e.g., top to bottom of the detector imaging area). The beam-on time 1302 may occur approximately one third into the readout of the first image frame 1310. The beam artifact 1380 can be seen in the null image 1312 for the first image frame 1310. In one embodiment, the signal in the beam artifact 1380 of the null image 1312 can be constant in the vertical direction during the beam on period, i.e., apart from a few rows of ramp up and ramp down. However, the magnitude in the horizontal direction in the beam artifact 1380 can depend on the combined signal across all photodiodes in each column.

As shown in FIG. 13, the second exposed image frame 1320 contains the remainder of the X-ray image data, e.g., the signal that was not read out during first frame 1310 because the beam was not on yet (beam-on 1302 occurred after those rows had been read out in the first frame 1310). This frame 1320 also contains the lag image data from the exposed signal read out during the first frame 1310. The third frame 1330 with image information is entirely a lag frame. The third image frame 1330 contains the first lag image data for the signal that was read out in the second image frame 1320 and the second lag image corresponding to the X-ray signal data read out in the first frame 1310. The fourth frame 1340 with image information is also a lag frame. For the exemplary case shown in FIG. 13, null images 1322, 1332, 1342 are not used for any image corrections. However, when the exposure (beam on) extends across multiple frames (e.g., longer than one frame, or starts in and goes beyond frame 1310), then the corresponding null images (e.g., 1322, 1332) can be used for correction.

Figure 14:
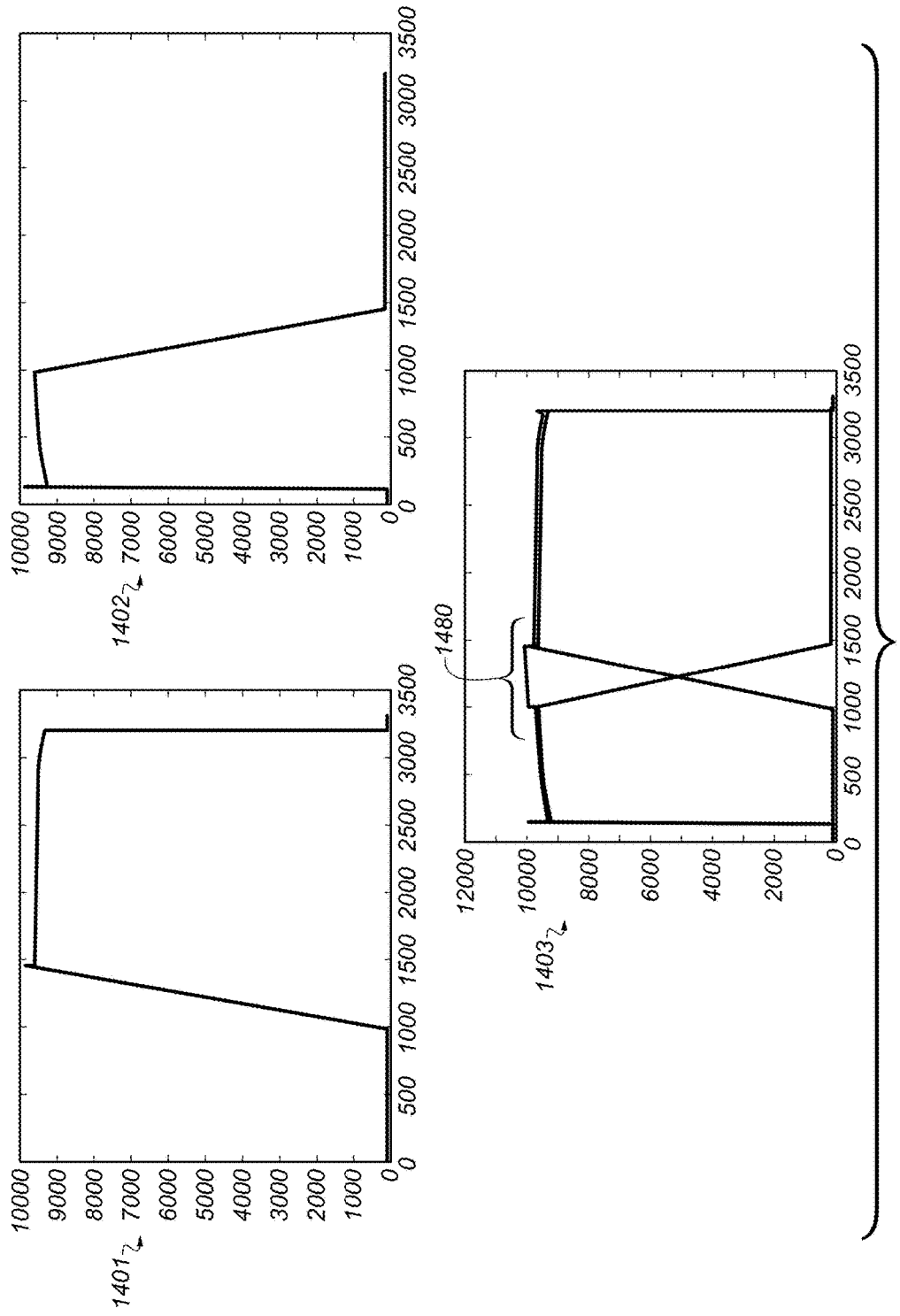
FIG. 14 is a diagram that shows image rows for flat field capture.

FIG. 14 is a diagram that shows graphs of composite image row signals for flat field capture similar to the capture of a human hand in FIG. 13. The signals from the first two frames (e.g., exposed image frame 1310 shown in the graph 1401 and 1320 shown in the graph 1402) are summed up, and the "pedestal" 1480 of the total signal during "beam on" can be seen in the graph 1403. The pedestal 1480 may represent the beam-on artifact 1380 shown in FIG. 13 or the error ε of FIG. 6B.

Figure 15:
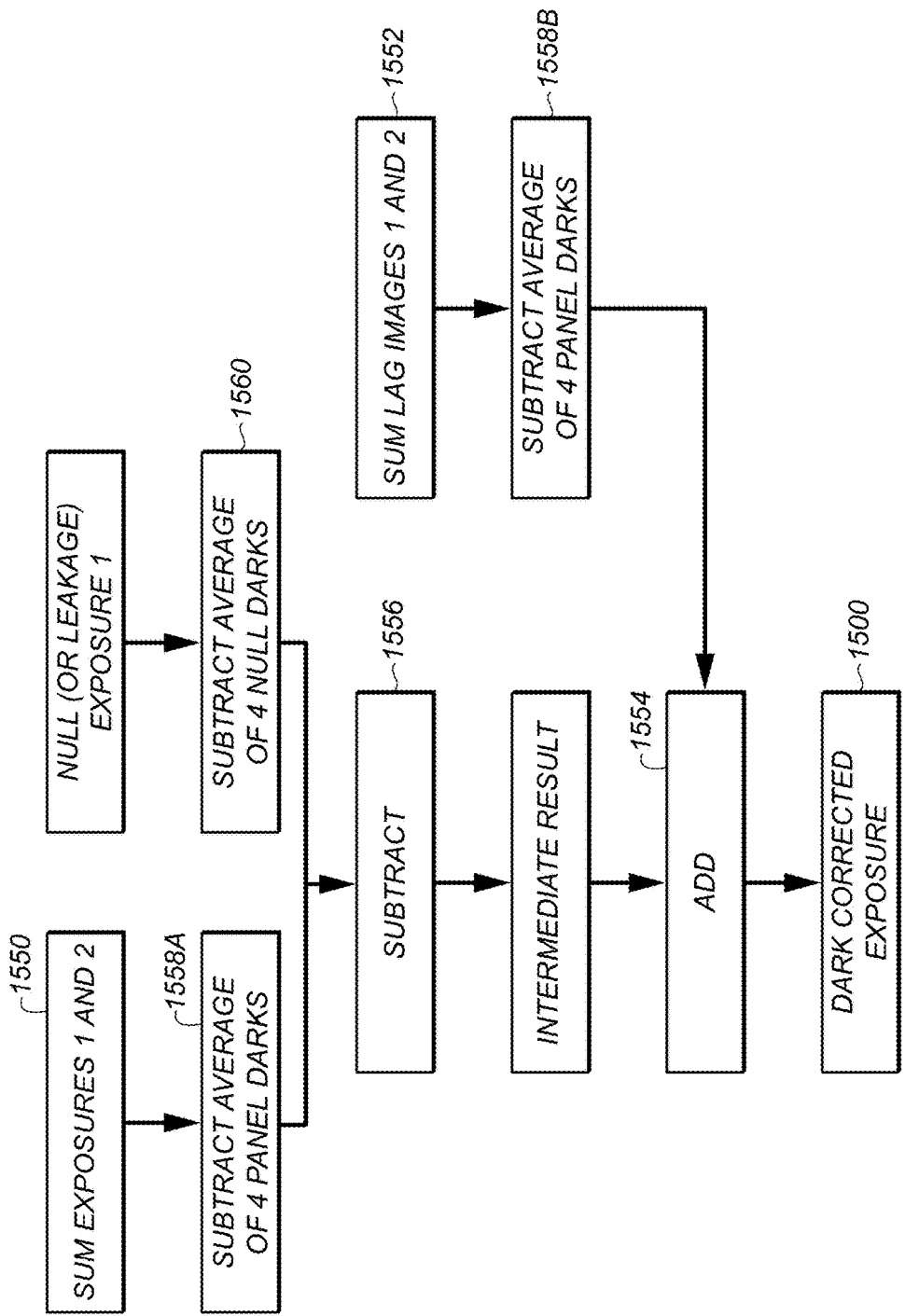
FIG. 15 is a flow chart that shows an exemplary image reconstruction and correction embodiment according to the application.

FIG. 15 is a flow chart that shows an exemplary image reconstruction and correction algorithm disclosed herein wherein the two image frames (e.g., 1310, 1320) containing the exposure information are added (operation block 1550) and the two subsequent lag frames (e.g., 1330, 1340) are added (operation block 1552) and then combined to form a reconstructed image 1500 (operation block 1554), while null image 1 (e.g., 1312) is subtracted (operation block 1556) to correct or reduce the pedestal (e.g., beam on artifact 1380). All null image (e.g., 1312) captures can be offset corrected (operation block 1560) using the last N dark images (e.g., combined, weighted or averaged) prior to the first null frame 1312. All image captures (e.g., 1310, 1320, 1330, 1340) are offset corrected (operation blocks 1558A, 1558B) using the last N dark images prior to the first exposed frame 1310. As shown in the algorithm of FIG. 15, the electronic noise from all added and subtracted frames can add up in quadrature.

Figure 16:
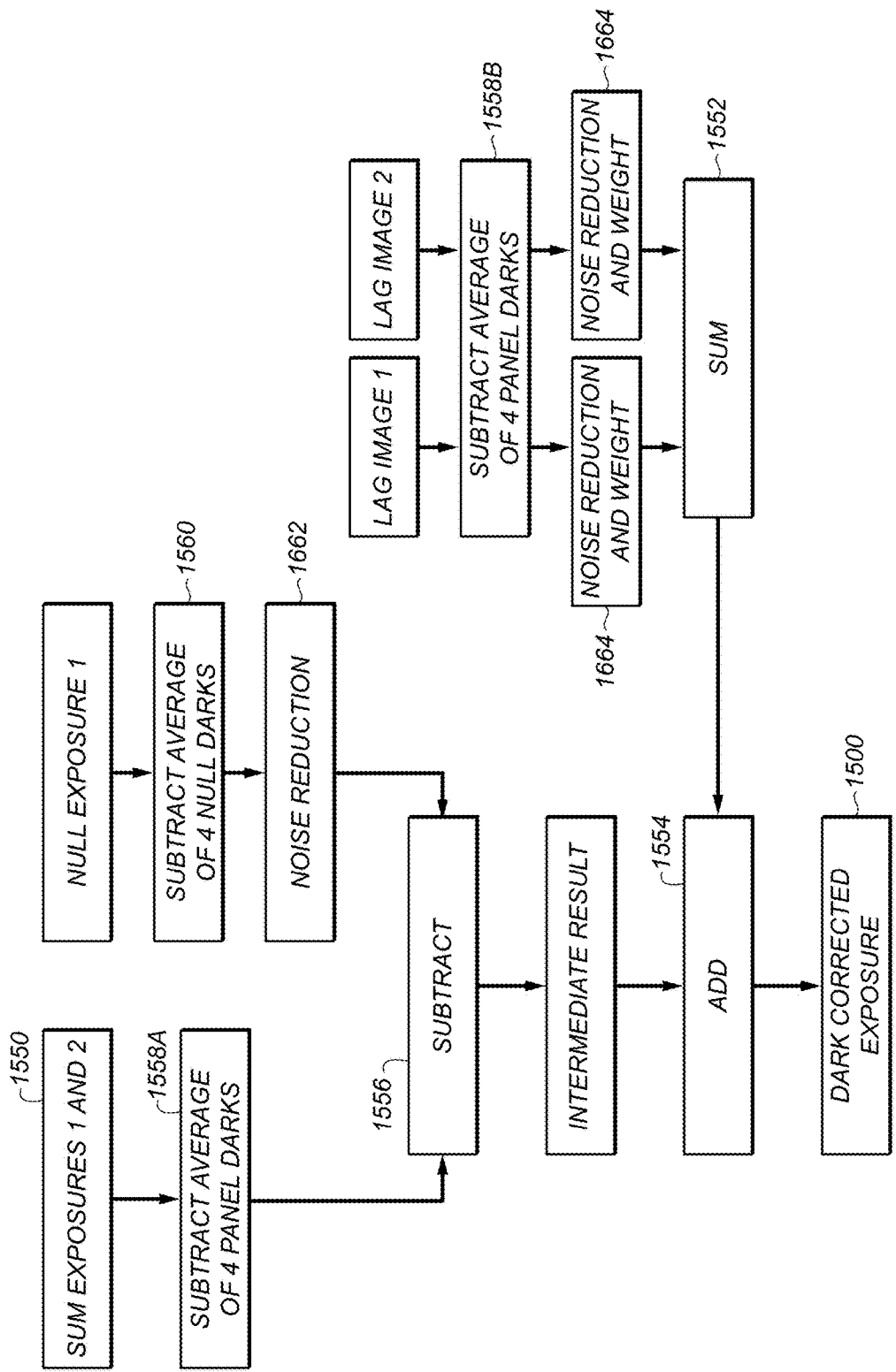
FIG. 16 is a flow chart that shows another exemplary image reconstruction and correction embodiment according to the application.

Certain exemplary system and/or method embodiments according to the application can provide the capability to reduce noise in the pre-dark corrected null and lag images before they are added or subtracted (e.g., weighted) from the images containing the signal. Furthermore, in accordance with certain exemplary embodiments, noise reduction can be considered for parts of the frames containing the exposure information (e.g., the dark section in the first image before the beam comes on could receive noise reduction). Noise in the final reconstructed and dark corrected image can be reduced in accordance with an exemplary embodiment shown in FIG. 16, wherein the steps of FIG. 15 are numbered similarly and alternative noise reduction steps 1662, and 1664 may be performed after step 1560 and 1558B, respectively. As shown in FIG. 16, all lag image captures (e.g., 1330, 1340) can be noise corrected (operation block 1664) using a first noise correction process (e.g., filter). Also all null images (e.g., 1312) can be noise corrected (operation block 1662) using a second noise correction process (e.g., filter) different from the first noise correction process (e.g., filter). In one embodiment, an optional different third noise correction process can be applied to all frames (e.g., 1310, 1320) containing the exposure information. As shown in FIG. 16 the electronic noise from all added and subtracted frames can add up to less than quadrature. Then, gain and defect correction can be added to the corrected image frame 1500.

In one embodiment, the first noise correction process 1664 and the second noise correction process 1662 are related to a frame or partial frame SNR, responsive to a frame or partial frame SNR or proportional to a frame or partial frame SNR, related to an image content amount, responsive to the image content amount or proportional to the image content amount. In one embodiment, the second noise correction process can include correcting a pre-exposed portion, an exposed portion and a post-exposed portion of the dark corrected at least one exposure leakage frame.

FIG. 17 is a diagram illustrating the image capture cycle of the DR detector 40 for a method of beam detection in one embodiment. When the DR detector 40 is not in the active beam detection mode, the detector may perform idle refresh cycles to conserve power, wherein all the critical device voltages are set at a default level and a readout controller is in a power down mode. The detector may perform alternating scrolling reset and integration, while integrated circuit devices may be set to a default state. When the detector receives a signal to initiate beam detection, at time 1702, the readout controller is powered up and the integrated circuit devices are activated. In this mode the detector simply performs cycles of integration 1714 and readout 1716, 1718. The integration step 1714 is optional. These blocks of integration and readout are represented by corresponding rectangles in FIG. 17. The readout scheme is used during this beam detection mode as shown in FIGS. 18A and 18B and described herein above with respect to at least FIGS. 7-8. The description corresponding to FIGS. 7-8 utilize the method shown in FIG. 18A (one image row read interleaved with one null row read) while the sequence illustrated in FIG. 17 utilizes the method shown in FIG. 18B (one image row read followed by two null row reads). Thus, data lines are read out three times for each row address, once with the gate line on and twice with the gate line off (all other timing is the same for the second and third readout). This means that the resulting image frame has three times the number of rows as the sensor. The additional rows are referred to as null1 and null2 rows.

After the readout controller powers up, the detector signals to the host, or acquisition control 34, that it is ready 1702. At this point the detector may have an initial offset map, which gets updated after each frame capture. The detector runs the beam on detection algorithm on all dark corrected image frames until a beam on event is found 1706 (or 1710 for a subsequent beam on detection). Five dark images may be captured after power up 1702 (the first dark image 1716 may be discarded, and the following four dark image captures may be averaged for offset correction) whereupon the detector signals to the host that it is ready to look for the beam on signal 1704. After establishing the beam on event the detector starts running the beam off detection algorithm. This algorithm finds the last frame containing exposure information 1722, i.e., the first frame after the end of the exposure. After finding this frame 1722, the detector takes two more lag images 1708 and performs image reconstruction. FIG. 17 illustrates the case where the X-ray exposure falls within a single frame 1706. This frame and the next frame 1722 contain exposure information, i.e., the image rows before "beam on" get read out in the second frame. In this case a total of four frames, 1706, 1722, 1708, shown in FIG. 17 are needed for the image reconstruction. The exposure can span multiple frames requiring more than four images for reconstruction. After capturing the second lag image for the current exposure event, the detector captures four dark frames to establish the new offset map and signals to the host 1709 that it is ready to look for the beam again. This cycle repeats, e.g., beam found at 1710, until the detector either receives an external command to exit beam detect mode 1712 or a timer started at the last beam detect event has expired and the detector returns to idle refresh mode, i.e., the readout controller enters power down mode 1724.

Figure 19:
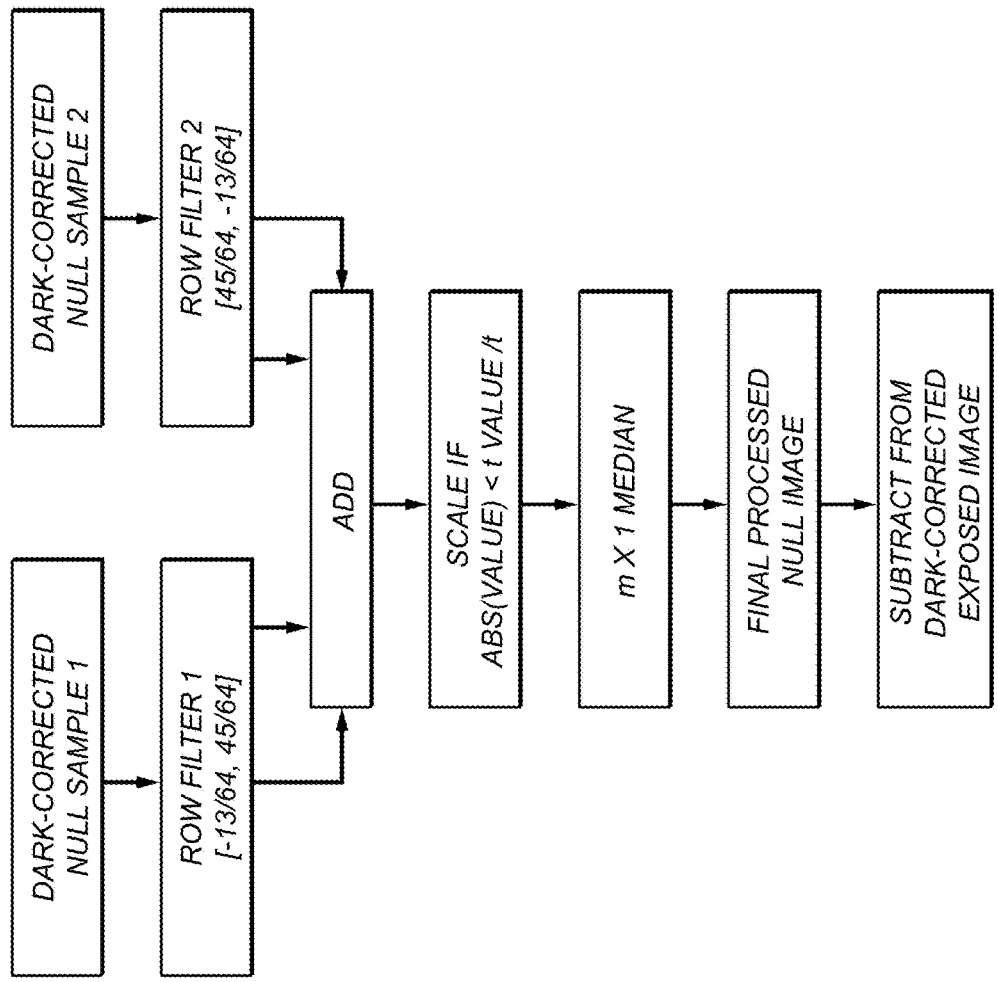
FIG. 19 is a flow chart of exemplary null image correction processing.

Image reconstruction may be undertaken as follows, with reference to FIG. 19 which illustrates null image processing for the readout scheme according to FIG. 18B by combining two null samples into a single null image, and noise reduction.

(1) Add all N dark corrected frames with exposure information. (The resulting image will be referenced as E.)

(2) Initialize the null image sum buffer $I_n$ to zero. Loop over all dark corrected null frames using index from i=1 ... N-1: if $M_{nmax,i} < t_{n,lo}$ discard the null frame; else for each row j≥2, weight the two null readouts for rows j-1 and j according to the following equation and save to row j of the combined null image $I_{n,i}$ (these calculations are done on a pixel by pixel basis in row j):

$$I_{n,i,j} = w_1 \cdot N1_{j-1} + w_2 \cdot N2_{j-1} + w_2 \cdot N1_j + w_1 \cdot N2_j$$

($N1_{j-1}$ is the first null read for row j-1, $N2_{j-1}$ is the second null read for row j-1, and similar nomenclature is applied to row j). The coefficients $w_1$ and $w_2$ must sum to 0.5 and preferably $w_2$ is greater than zero and $w_1$ is smaller than zero. The preferred settings are $w_1 = -13/64$ and $w_2 = 45/64$. Apply the following scaling to each pixel value CV of the image $I_{n,i}$: if $abs(CV) < t_{cv}$ $CV = CV \cdot abs(CV)/t_{cv}$. Then apply a 3×1 median filter to each pixel for further noise reduction. Add the fully corrected null frame $I_{n,i}$ to buffer $I_n$. The preferred settings for 16 bit systems are $t_{n,lo} = 8$ and $t_{cv} = 8$. These steps are shown in FIG. 19 for a single set of null captures.

(3) Calculate the offset corrected reconstructed exposure image $E_c$ as: $E_c = E - I_n$ (4) If the intensity of the beam is modulated during the beam on period, for example as a rectified sine wave, this manifests results in variations temporal variations of the leakage signal, e.g. ripple, and another correction must be applied. If $M_{nmax}$ for beam on frame > $t_{n,med}$ correct the ripple artifact. The preferred setting for 16 bit systems is $t_{n,med} = 120$. Execute the following algorithm (ripple suppression must be performed on all null frames captured during the beam on period):

```
If beam on frame == beam off frame
    {pass combined smoothed null image from step 2 for beam on
        frame to ripple suppression}
else if beam off frame > beam on frame + 1
    {pass combined smoothed null image from step 2 for beam on
        frame + 1 to ripple suppression}
else {if number of rows - j_on > j_off
            {pass combined smoothed null image from step 2 for beam
                on frame to ripple suppression}
     else
            {pass combined smoothed null image from step 2 for beam
                on frame + 1 to ripple suppression}
}
```

The beam off frame is one frame prior to the last frame containing exposure information that is identified by a beam off detection algorithm.

(5) The additional corrections in steps 5 and 6 compensate for any temporal mismatch between the leakage signal in the exposed row and the corresponding null rows when the beam turns on and off. This mismatch is observed in particular when the beam turns on or off very fast. If ($M_{nmax}$ for beam on frame > $t_{n,hi}$) AND ($j_{on}$ > top border-5) AND ($j_{on}$ < bottom border+5) correct the beam on artifact. One setting for 16 bit systems may be $t_{n,hi} = 200$.

(6) If ($M_{nmax}$ for beam off frame > $t_{n,hi}$) AND ($j_{off}$ > top border-5) AND ($j_{off}$ < bottom border+5) correct the beam off artifact.

(7) Initialize the lag sum buffer L to zero. Loop over the two additional dark corrected lag frames, N+1 and N+2: apply the following scaling to each pixel value CV of each lag frame: if $abs(CV) < t_L$ $CV = CV \cdot abs(CV)/t_L$. Then apply a 3×3 median filter to each pixel for further noise reduction. Add the fully corrected lag frame to buffer L. One setting for 16 bit systems may be $t_L = 40$.

(8) Calculate the fully offset corrected reconstructed exposure image $E_{c,final}$ as: $E_{c,final} = E_c + L$ (9) Run gain and defect correction, row noise removal, histogram shift and clipping.

Some X-ray scintillators, e.g., gadolinium oxysulfide (GOS), exhibit more light luminescence after absorbing the X-rays, whereas, for example cesium iodide has a fast response. A slow Scintillator response mitigates the beam artifacts addressed in steps 5 to 7. For detectors with a GOS scintillator, corrections in steps 5 to 7 may be skipped by entering higher threshold parameters for $t_{n,med}$ and $t_{n,hi}$.

"Beam on" and "beam off" conditions can be detected in an x-ray system, and when detected, null frames may be used for correction such as when the beam-on condition occurs during the null frame. Exemplary beam-on and beam-off condition detections may include the following. The pre-condition for beginning beam-detection can be calculating an average of N dark-frames captured just after the panel (e.g., DR detector) is powered up. In one embodiment, the apriori calculation of a defect map for the imager of the panel can be used. The apriori defect map can allow such outlier pixel values to be excluded from beam-on detection calculations, thereby reducing the sensitivity to panel defects and panel noise. It is also known that dark signal levels drift upward as panels warm up. One embodiment can operate to maintain a running average of some number of the most recent dark frames. Each time a frame is read-out, if no image is detected in the frame it can be determined to be another dark-frame, and as such should be used in the calculation of the running average of the last N dark frames. Such a running average dark frame can be an input to the beam-on detection methods described below.

Beam on can be detected by doing a line by line comparison of the mean signal level in the current line with the mean signal level of the corresponding line in the average dark frame. A threshold value can be calculated that takes into account the level of noise found in the N-frame dark average. In one embodiment, when the difference between the current line and the dark average exceeds the threshold value, a "beam-on" condition has been found within the current frame. In one embodiment, known defective pixel values can be excluded from the calculation of the mean signal level in the current line. In one embodiment, beam on can be detected using the exposure part or the leakage part (e.g., first frame 1310 or null frame 1312).

Figure 20:
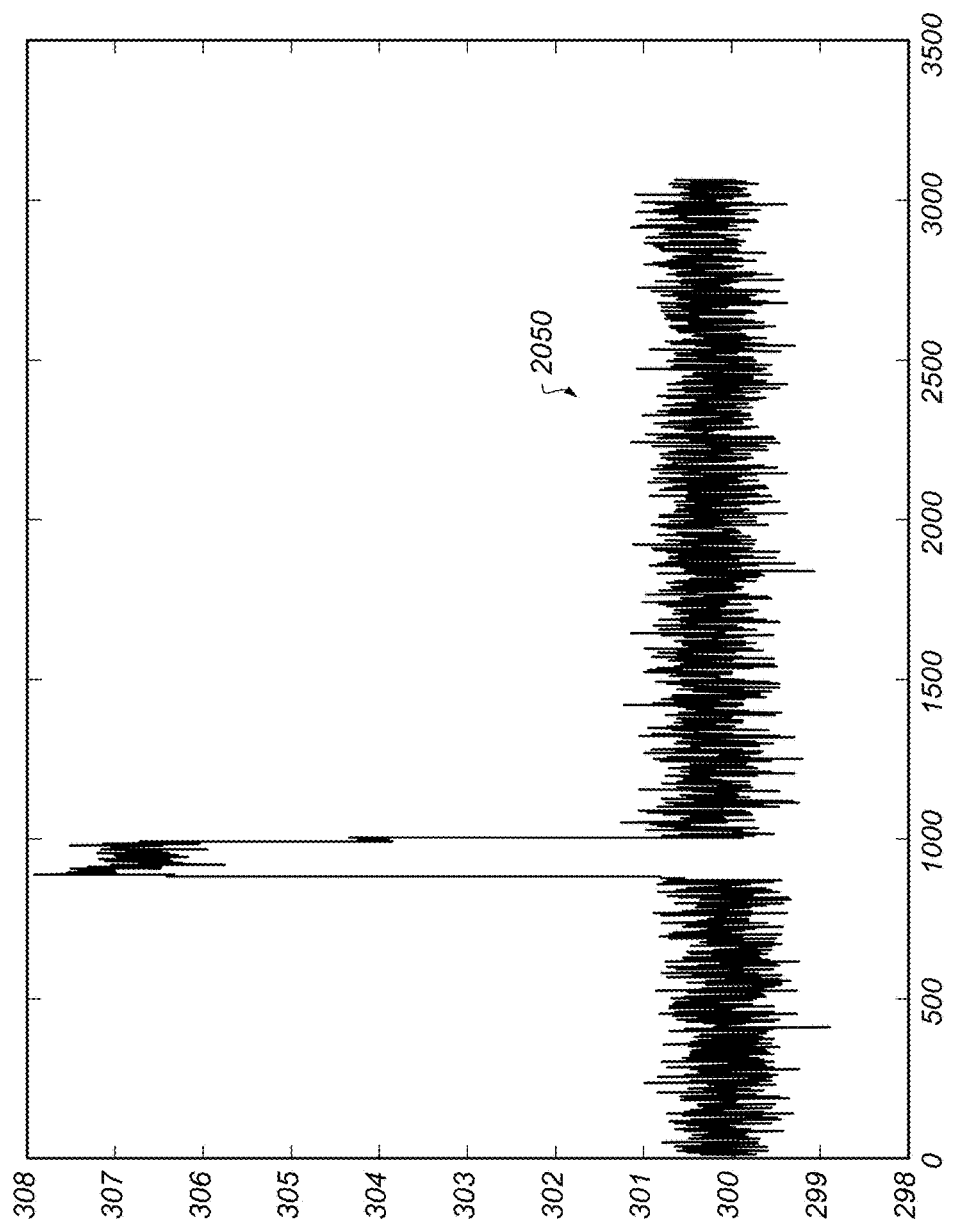
FIG. 20 is a diagram that shows an exemplary plot of leakage line sampling in a null image according to an embodiment of the application.

The beam-off event can be reliably detected by analyzing the line-average of the "null frame". This is shown in an example plot 2050 of a Null Line Average (or Leakage Line Average) as shown in FIG. 20. In the example plot 2050, it can be clearly seen that the beam has gone on and the beam has gone off during the first exposed frame. Once the "beam-on" frame is found, the mean signal level in the "null frame" can be used to determine a new threshold value to use in searching for the beam-off event. In different embodiments, when the mean signal-level drops below 75%, 50%, 25%, or 10% of the active signal level, then a beam-off condition has been found. In one embodiment, beam off can be detected using leakage data (e.g., null frame 1312).

In another alternative embodiment, the exposure leakage frame pedestal required for final image correction is approximated by calculation rather than measured directly. Such exemplary methods are useful because it makes the direct measurement of the exposure leakage frame unnecessary. This method is accomplished by first reconstructing a representative dark corrected full image frame from the partial images, dark images and lag images. Since in this embodiment an exposure leakage frame has not been obtained it is can be not used to remove the exposure leakage frame error from the representative image.

The reconstruction of an image is accomplished by adding all partial image frames and subsequent lag image frames together to form a reconstructed image using all the previously discussed noise reduction techniques. An operation is next applied to each column line of the reconstructed image to obtain the average value of all the pixels connected to any given column. The average value for each column can be obtained by summing the pixel values in a column and dividing by the number of rows in the detector frame. These calculated column average values are directly proportional to the magnitude of the exposure leakage generated in the column data lines during the X-ray beam exposure. To obtain a final representation of the actual exposure leakage frame the average values for each column must be scaled by a coefficient obtained by a separate calibration procedure that measures the actual leakage factor of the data lines in the particular type of detector being used. This single coefficient number will preferably be unique for that particular detector type.

The leakage coefficient for a detector type can be measured during the initial detector calibration process by placing the detector under a uniformly exposing X-ray beam that exposes the full image frame. The exposure intensity might vary from 50% to 100% of maximum or full scale exposure for the detector readout electronics. During the time period of the X-ray exposure event an exposure leakage frame is captured. Along with the exposure leakage frame several other frames must be captured as well and include: at least one dark leakage frame, an image frame and at least one dark image frame.

The exposure leakage frame must be first dark corrected by subtracting the dark leakage frame to obtain code values representative of the leakage signal on the data lines during exposure. Since the exposure is uniform over the detector surface area, the exposure leakage frame code values across all column lines can be around the same value. The captured image frame is next dark corrected by subtracting at least one dark frame to obtain the actual image code values produced by the X-ray exposure. Because the X-ray exposure was uniform over the detector surface the code values of the dark corrected image will also be approximately the same for all pixels. However, to obtain one representative code value from the image, the full image is averaged to obtain a mean code value for the image frame exposure. This mean code value can be designated as $I_{ave}$, the exposure leakage value obtained from the dark corrected exposure leakage frame can be designated as $U_{leak}$, and the X-ray beam exposure time can be designated as $t_{exp}$. The coefficient of leakage, $K_{leak}$, for the data lines of this particular detector can now be determined by the following equation:

$$(U_{leak}*t_{exp})/I_{ave}=K_{leak}$$

For example: if the leakage calibration exposure level is set to 80% of full scale, then for a 14 bit detector the exposure would be 0.8*16,384 or 13,107 code values. If the X-ray beam exposure period is 100 mS then exposure leakage frame data will have measurable values in those data lines that are readout during the 100 mS expose period. Therefore, if the average exposure leakage frame code value during this exposure was, for example 230, then the leakage coefficient for this detector would be calculated as:

$$230*0.1 \text{ sec}/13,107=0.00175$$

The reconstructed X-ray image that contains an exposure leakage frame pedestal error can now be corrected using this coefficient. As previously described, calculation of the exposure leakage frame from an actual X-ray image frame is accomplished by taking the column average value from the reconstructed image for each column and multiplying it by the measured detector leakage coefficient K. As an example: if a given column j has a summed average code value of 3498 and the X-ray beam exposure period was 100 ms then the exposure leakage frame error for this column j would be 3498*0.00175/$T_b$, where $T_b$ is the beam on time in seconds. In this example, $T_b$ was 100 mS, so the exposure leakage frame error for column j would be equal to [3498*0.00175/0.1] or 61 code values. This number is then subtracted from the image in the $j^{th}$ column at the rows where the X-ray beam exposure period coincided. This location is determined by identifying which rows were actively being readout during the exposure period between the detected beam on and beam off times. The column exposure leakage value must be subtracted only from rows that were actively readout during exposure.

Since it may occur that the beam on time may be longer than the readout time of one image frame, that is the beam exposure period is longer than the frame readout time, there may be some rows that were successively readout from one frame to the next frame and that have exposure leakage error in both of the readout values. This means that when the partial image frames are reconstructed there might be certain rows that must have the exposure leakage value subtracted more than once. As an example, if it was determined that rows n through row n+234 were readout twice during beam exposure, the calculated exposure leakage error would be 2*61 or 122 for rows n through n+234 for the column j data line.

Calculation of the column leakage frame error codes are repeated for all column lines to obtain the exposure leakage frame error introduced into the image during the readout process. To remove the exposure leakage frame error from the reconstructed image the calculated column leakage error is subtracted column by column from the reconstructed image rows for those rows that were readout during the time when the X-ray exposing beam was on. Therefore, it is necessary to establish what row was being readout when the beam on condition was detected and what final row was being readout when the beam off condition was detected.

A beam off event can be detected by comparing image line data values concurrently with the readout process after the beam on event has been detected. In such exemplary methods, each particular image line of data is compared to the previous readout frame of the exact same image line to determine if the present readout value in the current image line is greater than, less than or approximately the same as the value readout in the previous frame. If the beam was on in the previous frame when a particular image line was readout and is still on during the next frame during readout of the same line then the values will be approximately the same.

Having determined when the beam-off event occurred, when to stop reading out exposed image data can be determined. It is the nature of continuous readout that image data can be read out from the line at which the beam came on until one full frame beyond the time of the beam-off event (e.g., to capture a full exposed image). From the null image, it was determined that the beam went off during the first image frame (e.g., 1310). However, the presence of image data clearly continues until the corresponding line in the following image frame (e.g., image frame 1320).

Second, noise reduction can be applied to the null image. Various methods can be used. In one embodiment, a median filter or other low pass filter can be applied to the image. The filter preferably can maintain the top and bottom edges in the image associated with the beam on event and beam off event. In one embodiment, exemplary filters are preferably wider in the vertical direction compared with the horizontal direction.

In one alternative embodiment, the exact locations of "beam on" and "beam off" can be detected, and a column average can be calculated between the "beam on" and "beam off" event. Then, the column average may be subtracted from the corresponding image containing the signal. Further, noise reduction can be applied to the lag images, for example, using two-dimensional low pass filters. The low-pass filtered lag image is preferably weighted by the normalized lag signal itself, so that low lag signals (e.g., associated with low dose) are de-weighted and add even less noise, while the full magnitude of higher lag signals is maintained or added.

As exemplified herein, the image readout process for a DR detector system may be performed after an x-ray expose-integration period has occurred. The purpose of the image readout operation is to acquire x-ray exposed patient image data from the DR detector's pixel array produced by the expose-integration process. The image information may be sequentially read out from each pixel row of the detector array into an internal image buffer, as described herein. The first exposed image readout may be immediately followed by a second non-exposed-integration period, which may be performed during an interval when there is no incident x-ray radiation impinging the sensor array of the DR detector. Since no x-ray radiation is present during the non-exposed-integration period, there is no new image information in the second read out image (e.g., lag image 955). However, because the first image readout operation leaves a small percentage of signal data remaining in the detector pixel array, the second readout operation recovers this left over signal data. The second read out image is typically referred to as image lag or simply a dark image. These steps may be repeated to obtain a third non-exposed-integration operation image without x-ray radiation to obtain a second dark image frame. A post processing operation may be performed on the set of acquired image frames, e.g., the exposed image having one or two frames, the first non-exposed dark image frame and the second non-exposed dark image frame may be added together or otherwise processed, to produce the final artifact free DR detector image.

The complementary set of image data and null row data may then be processed to determine the magnitude of any extraneous signal present on the data lines during the image readout operation, as described herein. In one embodiment, when extraneous signal magnitude is above a certain threshold, it may be compensated or removed from the image data by a process of combining (e.g., subtracting, weighting) the null row data from the image readout data. Subtracting the null row data from the image readout data may reduce or remove extraneous signal noise from the image readout data because Null Row data does not contain image data information from the pixel sensor array.

One caveat to such methods is that because the image readout operation is not perfectly simultaneous with the null row read operation, there may be some error in any measured extraneous signal if the frequency components of the extraneous signal are a prescribed amount greater than (e.g., twice) the readout sampling frequency of the null row read operation. This condition violates the Nyquist sampling criterion and may produce an erroneous aliased signal in the null row read data. If these aliased signals are present then it may be difficult to remove the extraneous signals from the image data by subtracting the two image sets.

When it is likely that extraneous signal frequencies are higher than the readout sampling frequency an alternate method may be used. This method implements a series of null row read operations that are performed before an x-ray exposure process has been initiated and may be used to detect if there is extraneous signal noise from external low frequency magnetic fields present on the data lines before the x-ray exposure and image readout operation has started. In this case, successive null now reads are performed and the digitized data line signals are stored into a temporary row buffer similar to the buffers shown in FIG. 8. A real time digital processing algorithm is then applied to the data from the null row read operation to determine if any extraneous signal is present by comparing a magnitude, or intensity, of the data obtained. While the frequencies of external magnetic fields will most likely be greater than the null row read sampling frequency the aliased signals in the null row read data is not a concern because this method only needs to detect that an extraneous signal was present.

According to exemplary embodiments, null row read data may be used in several ways to detect, compensate for, reduce and prevent extraneous signals from interfering with the standard image readout operation. One null row read process embodiment may be used to detect the presence of extraneous signals (e.g., null row read data) before an x-ray exposure occurs. As discussed previously, when the image readout operation is performed concurrently with an x-ray radiation exposure operation an extraneous signal is impressed on all data lines in the pixel array sensor. The magnitude of the extraneous signal on the individual data line is dependent on the number of photons at each of the photodiode sites along the entire data line and this is dependent on the intensity of x-ray fluence impinging the scintillator at the photodiode sites along the length of the data line.

Exemplary digital processing algorithms to detect extraneous noise on the data lines may be implemented in firmware and software using high speed digital processing electronics, such as Field Programmable Gate Arrays (FPGAs) and CPUs, which are placed internal to the DR detector system. If any extraneous signal is detected, this condition may be communicated by the DR detector system hardware and software to the operator through a visible/audible alert at the system console. The operator may then take preventative steps to remove the source of magnetic fields to avoid interference with the DR detector system image readout operation. This is especially useful for portable wireless DR detector systems which, when used by mobile x-ray units, may be operated in many different locations within a hospital or clinic.

When the image readout operation is complemented with an interleaved null row read operation according to embodiments described herein, means may be provided to perform the image readout operation during the x-ray exposure period and address or remove the inherent leakage current image artifact produced by parasitic capacitances in the pixel array sensor.

In one exemplary embodiment, an error produced by extraneous leakage current on the data line may be determined independent and separate from the image data by following an image row readout process with a corresponding null row read process. Since the leakage current is present on the data lines even when the TFTs are all turned off this provides a way to measure the extraneous leakage current right after at each image row read. Since the leakage current is measured separately and independently, it may be subtracted from the image data in a post process operation. Further, because the extraneous leakage current onto the data lines effectively remains at a constant level during the x-ray exposure, there is no danger that aliasing error will be present in the null row read data.

Using the methods described herein makes possible the detection of interference caused by low frequency magnetic fields that would degrade final image quality and thereby detecting and prevent such occurrence by alerting the operator of a DR detector system. Additionally, exemplary methods and system embodiments described herein may provide a capability to perform image readout operations during the x-ray expose operations and to be able to measure/monitor induced extraneous signals and compensate for or remove induced extraneous signals from the image data set to obtain final output images that are of clinical diagnostic quality.

As will be appreciated by one skilled in the art, the present invention may be embodied as a system, method, or computer program product. Accordingly, an embodiment of the present invention may be in the form of an entirely hardware embodiment, an entirely software embodiment (including firmware, resident software, micro-code, and other suitable encodings) or an embodiment combining software and hardware aspects that may all generally be referred to herein as a "circuit" or "system." Furthermore, the present invention may take the form of a computer program product embodied in a computer-readable storage medium, with instructions executed by one or more computers or host processors. This medium may comprise, for example: magnetic storage media such as a magnetic disk (such as a hard drive or a floppy disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

While the invention has been illustrated with respect to one or more implementations, alterations and modifications may be made to the illustrated examples without departing from the spirit and scope of the appended claims. In addition, while a particular feature of the invention may have been disclosed with respect to only one of several implementations, such feature may be combined with one or more other features of the other implementations as may be desired and advantageous for any given or particular function. The term "at least one of" is used to mean one or more of the listed items may be selected. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of radiographic image correction for a digital radiographic detector, the method comprising:
    obtaining an exposed image frame;
    obtaining an unexposed image frame;
    combining the exposed image frame and the unexposed image frame to form a corrected image frame;
    obtaining an exposed leakage frame;
    obtaining an unexposed leakage frame;
    combining the exposed leakage frame and the unexposed leakage frame to form a conditioned null frame; and
    combining the corrected image frame and the conditioned null frame to form a final corrected radiographic image.

2. The method of claim 1, wherein the step of obtaining an unexposed image frame comprises capturing and averaging two or more unexposed image frames to obtain the unexposed image frame, and wherein the step of obtaining an unexposed leakage frame comprises capturing and averaging two or more unexposed leakage frames to obtain the unexposed leakage frame.

3. The method of claim 1, wherein the step of combining the exposed image frame and the unexposed image frame comprises subtracting the unexposed image frame from the exposed image frame.

4. The method of claim 3, wherein the step of combining the exposed leakage frame and the unexposed leakage frame comprise: subtracting the unexposed leakage frame from the exposed leakage frame.

5. The method of claim 4, wherein the step of combining the corrected image frame and the conditioned null frame comprises subtracting the conditioned null frame from the corrected image frame.

6. The method of claim 1, wherein the exposed image frame comprises an X-ray beam start.

7. The method of claim 1, wherein the step of combining the corrected image frame and the conditioned null frame to form a final corrected radiographic image is performed in the digital radiographic detector.

8. A method of image correction for a digital radiographic detector, the method comprising:
   obtaining at least one exposed image data frame including activating gate lines to read out the at least one exposed image data frame row by row;
   obtaining at least one unexposed dark frame including activating the gate lines to read out the at least one unexposed dark frame row by row;
   obtaining at least one exposed leakage frame including keeping the gate lines off to read out the at least one exposed leakage frame row by row;
   obtaining at least one unexposed dark leakage frame including keeping the gate lines off to read out the at least one unexposed dark leakage frame row by row;
   correcting the at least one exposed image data frame using the at least one unexposed dark frame;
   correcting the at least one exposed leakage frame using the at least one unexposed dark leakage frame; and
   combining the corrected at least one exposed image data frame and the corrected at least one exposed leakage frame to obtain a corrected image frame.

9. The method of claim 8, further comprising determining x-ray beam on or x-ray beam off using row-to-row comparison of the at least one exposed image data frame.

10. The method of claim 8, wherein the step of obtaining at least one unexposed dark frame comprises capturing and averaging two or more unexposed dark frames to obtain the at least one unexposed dark frame, and wherein the step of obtaining at least one unexposed dark leakage frame comprises capturing and averaging two or more unexposed dark leakage frames to obtain the at least one unexposed dark leakage frame.

11. The method of claim 8, wherein the step of correcting the at least one exposed image data frame comprises subtracting the at least one unexposed dark frame from the at least one exposed image data frame.

12. The method of claim 11, wherein the step of correcting the at least one exposed leakage frame comprises subtracting the at least one unexposed dark leakage frame from the at least one exposed leakage frame.

13. The method of claim 12, wherein the step of combining the corrected at least one exposed image data frame and the corrected at least one exposed leakage frame comprises subtracting the at least one exposed leakage frame from the corrected at least one exposed image data frame.

14. The method of claim 8, wherein the at least one exposed image data frame comprises an X-ray beam start.

15. The method of claim 8, wherein the method is performed in the digital radiographic detector.

16. A digital radiographic detector comprising a program of instructions configured to be executed on a processor in the digital radiographic detector, the program of instructions causing the digital radiographic detector to perform the steps of:
   obtaining an exposed image frame;
   obtaining an unexposed image frame;
   combining the exposed image frame and the unexposed image frame to form a corrected image frame;
   obtaining an exposed leakage frame;
   obtaining an unexposed leakage frame;
   combining the exposed leakage frame and the unexposed leakage frame to form a conditioned null frame; and
   combining the corrected image frame and the conditioned null frame to form a final corrected radiographic image.

17. The method of claim 16, wherein the step of combining the exposed image frame and the unexposed image frame comprises subtracting the unexposed image frame from the exposed image frame.

18. The method of claim 17, wherein the step of combining the exposed leakage frame and the unexposed leakage frame comprises subtracting the unexposed leakage frame from the exposed leakage frame.

19. The method of claim 18, wherein the step of combining the corrected image frame and the conditioned null frame comprises subtracting the conditioned null frame from the corrected image frame.

\* \* \* \* \*

UNITED STATES PATENT AND TRADEMARK OFFICE
CERTIFICATE OF CORRECTION

PATENT NO. : 10,039,516 B2
APPLICATION NO. : 14/534737
DATED : August 7, 2018
INVENTOR(S) : Karin Toepfer et al.

Page 1 of 1

It is certified that error appears in the above-identified patent and that said Letters Patent is hereby corrected as shown below:

In the Specification

Column 12, Line 13  Replace "the error data E as shown in FIG. 6B." with --the error data $\varepsilon$ as shown in FIG. 6B.--

Signed and Sealed this
Twenty-fourth Day of September, 2019

Andrei Iancu
*Director of the United States Patent and Trademark Office*